(12) United States Patent
Werneth et al.

(10) Patent No.: US 6,576,001 B2
(45) Date of Patent: Jun. 10, 2003

(54) LUMEN DESIGN FOR CATHETER

(75) Inventors: Randell L. Werneth, San Diego, CA (US); Kevin P. Gilmartin, Encinitas, CA (US); Steven A. Yon, San Diego, CA (US); Juan C Lasheras, La Jolla, CA (US); John D Dobak, III, La Jolla, CA (US)

(73) Assignee: Innercool Therapies, Inc., San Diego, CA (US)

( * ) Notice: Subject to any disclaimer, the term of this patent is extended or adjusted under 35 U.S.C. 154(b) by 1 day.

(21) Appl. No.: 10/005,056

(22) Filed: Dec. 3, 2001

(65) Prior Publication Data

US 2002/0049484 A1 Apr. 25, 2002

Related U.S. Application Data

(62) Division of application No. 09/519,022, filed on Mar. 3, 2000, now Pat. No. 6,379,378.

(51) Int. Cl.$^7$ .................................................. A61F 7/00
(52) U.S. Cl. ..................... 607/104; 607/105; 604/43; 604/264
(58) Field of Search ........................... 607/96, 104–106; 606/20–23, 27, 28; 604/43, 264

(56) References Cited

U.S. PATENT DOCUMENTS

| 1,011,606 A | 12/1911 | Fulton |
| 2,148,541 A | 2/1939 | Dierker |

(List continued on next page.)

FOREIGN PATENT DOCUMENTS

| AU | 730835 B2 | 3/2001 |
| AU | 739996 B2 | 10/2001 |

(List continued on next page.)

OTHER PUBLICATIONS

Ambrus: The Biphasic Nature and Temperature Dependence of the Activation of Human Plasminogen by Urokinase; May 1979; pp. 339–347; Research Communications in Chemical Pathology and Pharmacology, vol. 24, No. 2.

(List continued on next page.)

*Primary Examiner*—Roy D. Gibson
(74) *Attorney, Agent, or Firm*—Procopio, Cory, Hargreaves & Savitch, LLP

(57) ABSTRACT

The invention provides a device for heating or cooling a surrounding fluid in a feeding vessel and a method of manufacturing the same. The device includes a catheter assembly capable of insertion to a selected blood vessel in the vascular system of a patient. The assembly includes an elongated catheter body, a heat transfer element located at a distal portion of the catheter body and including an interior, an elongated supply lumen adapted to deliver a working fluid to the interior of the heat transfer element and having a hydraulic diameter, an elongated return lumen adapted to return a working fluid from the interior of the heat transfer element and having a hydraulic diameter, and wherein the ratio of the hydraulic diameter of the return lumen to the hydraulic diameter of the supply lumen is substantially equal to 0.75. The method of manufacturing the catheter assembly involves extruding an elongated catheter body; locating a heat transfer element including an interior at a distal portion of the catheter body; extruding an integrated elongated bi-lumen member including a first lumen adapted to receive a guide wire and a second lumen having a hydraulic diameter, the second lumen comprising either a supply lumen to deliver a working fluid to an interior of the heat transfer element or a return lumen to return a working fluid from the interior of the heat transfer element; and providing the integrated bi-lumen member substantially within the elongated catheter body so that a third lumen having a hydraulic diameter is formed, the third lumen comprising either a supply lumen to deliver a working fluid to an interior of the heat transfer element or a return lumen to return a working fluid from the interior of the heat transfer element and the ratio of the second lumen hydraulic diameter to the third lumen hydraulic diameter is substantially equal to 0.75.

9 Claims, 22 Drawing Sheets

U.S. PATENT DOCUMENTS

| | | |
|---|---|---|
| 2,308,484 A | 1/1943 | Auzin et al. |
| 2,374,609 A | 4/1945 | McCollum |
| 2,466,042 A | 4/1949 | Reich et al. |
| 2,615,686 A | 10/1952 | Davidson |
| 2,672,032 A | 3/1954 | Towse |
| 2,913,009 A | 11/1959 | Kuthe |
| 3,125,096 A | 3/1964 | Antiles et al. |
| 3,298,371 A | 1/1967 | Lee |
| 3,425,419 A | 2/1969 | Dato |
| 3,460,538 A | 8/1969 | Armstrong |
| 3,504,674 A | 4/1970 | Swenson et al. |
| 3,604,419 A | 9/1971 | Diskin |
| 3,612,175 A | 10/1971 | Ford et al. |
| 3,768,484 A | 10/1973 | Gawura |
| 3,839,621 A | 10/1974 | Hariu |
| 3,865,116 A | 2/1975 | Brooks |
| 3,888,259 A | 6/1975 | Miley |
| 3,971,383 A | 7/1976 | Van Gerven |
| 4,038,519 A | 7/1977 | Foucras |
| 4,153,048 A | 5/1979 | Magrini |
| 4,160,455 A | 7/1979 | Law |
| 4,190,033 A | 2/1980 | Foti |
| 4,216,767 A | 8/1980 | Aosiro |
| 4,231,425 A | 11/1980 | Engstrom |
| 4,241,729 A | 12/1980 | Aoshiro |
| 4,275,734 A | 6/1981 | Mitchiner |
| 4,298,006 A | 11/1981 | Parks |
| 4,318,722 A | 3/1982 | Altman |
| 4,323,071 A | 4/1982 | Simpson et al. |
| 4,427,009 A | 1/1984 | Wells et al. |
| 4,445,500 A | 5/1984 | Osterholm |
| 4,464,172 A | 8/1984 | Lichtenstein |
| 4,483,341 A | 11/1984 | Witteles |
| 4,484,586 A | 11/1984 | McMickle et al. |
| 4,502,286 A | 3/1985 | Okada et al. |
| 4,569,355 A | 2/1986 | Bitterly |
| 4,581,017 A | 4/1986 | Sahota |
| 4,602,642 A | 7/1986 | O'Hara et al. |
| 4,655,746 A | 4/1987 | Daniels et al. |
| 4,672,962 A | 6/1987 | Hershenson |
| 4,731,072 A | 3/1988 | Aid |
| 4,745,922 A | 5/1988 | Taylor |
| 4,747,826 A | 5/1988 | Sassano |
| 4,748,979 A | 6/1988 | Hershenson |
| 4,750,493 A | 6/1988 | Brader |
| 4,762,129 A | 8/1988 | Bonzel |
| 4,762,130 A | 8/1988 | Fogarty et al. |
| 4,781,799 A | 11/1988 | Herbert, Jr. et al. |
| 4,817,624 A | 4/1989 | Newbower |
| 4,820,349 A | 4/1989 | Saab |
| 4,860,744 A | 8/1989 | Johnson et al. |
| 4,883,455 A | 11/1989 | Leonard |
| 4,894,164 A | 1/1990 | Polaschegg |
| 4,904,237 A | 2/1990 | Janese |
| 4,920,963 A | 5/1990 | Brader |
| 4,951,677 A | 8/1990 | Crowley et al. |
| 4,964,409 A | 10/1990 | Tremulis |
| 5,000,734 A | 3/1991 | Boussignac |
| 5,002,531 A | 3/1991 | Bonzel |
| 5,014,695 A | 5/1991 | Benak et al. |
| 5,018,521 A | 5/1991 | Campbell |
| 5,019,075 A | 5/1991 | Spears et al. |
| 5,024,668 A | 6/1991 | Peters et al. |
| 5,041,089 A | 8/1991 | Mueller et al. |
| 5,046,497 A | 9/1991 | Millar |
| 5,078,713 A | 1/1992 | Varney |
| 5,089,260 A | 2/1992 | Hunter et al. |
| 5,092,841 A | 3/1992 | Spears |
| 5,106,360 A | 4/1992 | Ishiwara et al. |
| 5,106,368 A | 4/1992 | Uldall et al. |
| 5,108,390 A | 4/1992 | Potocky et al. |
| RE33,911 E | 5/1992 | Samson et al. |
| 5,110,721 A | 5/1992 | Anaise et al. |
| 5,112,438 A | 5/1992 | Bowers |
| 5,117,822 A | 6/1992 | Laghi |
| 5,135,599 A * | 8/1992 | Martin et al. ............... 156/294 |
| 5,147,355 A | 9/1992 | Friedman et al. |
| 5,149,321 A | 9/1992 | Klatz et al. |
| 5,150,706 A | 9/1992 | Cox et al. |
| 5,151,100 A | 9/1992 | Abele et al. |
| 5,151,578 A | 9/1992 | Phillips |
| 5,180,364 A | 1/1993 | Ginsburg |
| 5,190,539 A | 3/1993 | Fletcher et al. |
| 5,191,883 A | 3/1993 | Lennox et al. |
| 5,196,024 A | 3/1993 | Barath |
| 5,211,631 A | 5/1993 | Sheaff |
| 5,234,405 A | 8/1993 | Klatz et al. |
| 5,236,908 A | 8/1993 | Gruber et al. |
| 5,246,421 A | 9/1993 | Saab |
| 5,248,312 A | 9/1993 | Langberg |
| 5,250,070 A | 10/1993 | Parodi |
| 5,257,977 A | 11/1993 | Eshel |
| 5,264,260 A | 11/1993 | Saab |
| 5,267,341 A | 11/1993 | Shearin |
| 5,269,369 A | 12/1993 | Faghri |
| 5,269,749 A | 12/1993 | Koturov |
| 5,269,758 A | 12/1993 | Taheri |
| 5,281,213 A | 1/1994 | Milder et al. |
| 5,281,215 A | 1/1994 | Milder |
| 5,295,949 A | 3/1994 | Hathaway |
| 5,306,261 A | 4/1994 | Alliger et al. |
| 5,310,440 A | 5/1994 | Zingher |
| 5,322,514 A | 6/1994 | Steube et al. |
| 5,322,515 A | 6/1994 | Karas et al. |
| 5,322,518 A | 6/1994 | Schneider et al. |
| 5,326,165 A | 7/1994 | Walthall et al. |
| 5,326,166 A | 7/1994 | Walthall et al. |
| 5,330,435 A | 7/1994 | Vaillancourt |
| 5,330,519 A | 7/1994 | Mason et al. |
| 5,334,193 A | 8/1994 | Nardella |
| 5,342,301 A | 8/1994 | Saab |
| 5,342,621 A | 8/1994 | Eury |
| 5,344,436 A | 9/1994 | Fontenot et al. |
| 5,354,272 A | 10/1994 | Swendson et al. |
| 5,358,486 A | 10/1994 | Saab |
| 5,364,364 A | 11/1994 | Kasvikis et al. |
| 5,365,750 A | 11/1994 | Greenthal |
| 5,368,591 A | 11/1994 | Lennox et al. |
| 5,374,245 A * | 12/1994 | Mahurkar ................ 604/43 |
| 5,383,854 A | 1/1995 | Safar et al. |
| 5,383,918 A | 1/1995 | Panetta |
| 5,395,314 A | 3/1995 | Klatz et al. |
| 5,395,331 A | 3/1995 | O'Neill et al. |
| 5,403,281 A | 4/1995 | O'Neill et al. |
| 5,405,371 A | 4/1995 | Augustine et al. |
| 5,417,686 A | 5/1995 | Peterson et al. |
| 5,423,745 A | 6/1995 | Todd et al. |
| 5,423,807 A | 6/1995 | Milder |
| 5,433,740 A | 7/1995 | Yamaguchi |
| 5,437,673 A | 8/1995 | Baust et al. |
| 5,443,456 A | 8/1995 | Alliger et al. |
| 5,462,521 A | 10/1995 | Brucker et al. |
| 5,486,159 A * | 1/1996 | Mahurkar ................ 604/6.16 |
| 5,486,204 A | 1/1996 | Clifton |
| 5,486,208 A | 1/1996 | Ginsburg |
| 5,496,271 A | 3/1996 | Burton et al. |
| 5,496,311 A | 3/1996 | Abele et al. |
| 5,499,973 A | 3/1996 | Saab |
| 5,520,682 A | 5/1996 | Baust et al. |
| 5,531,776 A | 7/1996 | Ward et al. |
| 5,536,247 A | 7/1996 | Thornton |

| Patent No. | Date | Inventor(s) |
|---|---|---|
| 5,545,133 A | 8/1996 | Burns et al. |
| 5,545,708 A | 8/1996 | Onwunaka et al. |
| 5,549,559 A | 8/1996 | Eshel |
| 5,554,119 A | 9/1996 | Harrison et al. |
| 5,558,644 A | 9/1996 | Boyd et al. |
| 5,569,195 A | 10/1996 | Saab |
| 5,573,532 A | 11/1996 | Chang et al. |
| 5,578,008 A | 11/1996 | Hara |
| 5,584,804 A | 12/1996 | Klatz et al. |
| 5,588,438 A | 12/1996 | McKown et al. |
| 5,591,162 A | 1/1997 | Fletcher et al. |
| 5,620,480 A | 4/1997 | Rudie |
| 5,622,182 A | 4/1997 | Jaffe |
| 5,624,342 A | 4/1997 | Younger |
| 5,624,392 A | 4/1997 | Saab |
| 5,630,837 A | 5/1997 | Crowley |
| 5,643,197 A | 7/1997 | Brucker et al. |
| 5,647,051 A | 7/1997 | Neer |
| 5,653,692 A | 8/1997 | Masterson et al. |
| 5,676,693 A | 10/1997 | LaFontaine |
| 5,709,654 A | 1/1998 | Klatz et al. |
| 5,713,941 A | 2/1998 | Robins et al. |
| 5,716,386 A | 2/1998 | Ward et al. |
| 5,733,318 A | 3/1998 | Augustine |
| 5,733,319 A | 3/1998 | Neilson et al. |
| 5,735,809 A | 4/1998 | Gorsuch |
| 5,797,878 A | 8/1998 | Bleam |
| 5,799,661 A | 9/1998 | Boyd et al. |
| 5,800,480 A | 9/1998 | Augustine et al. |
| 5,800,483 A | 9/1998 | Vought |
| 5,800,486 A | 9/1998 | Thome et al. |
| 5,800,488 A | 9/1998 | Crockett |
| 5,800,493 A | 9/1998 | Stevens et al. |
| 5,800,516 A | 9/1998 | Fine et al. |
| 5,807,391 A | 9/1998 | Wijkamp |
| 5,820,593 A | 10/1998 | Safar et al. |
| 5,824,030 A | 10/1998 | Yang et al. |
| 5,827,222 A | 10/1998 | Klatz et al. |
| 5,827,237 A | 10/1998 | Macoviak et al. |
| 5,827,269 A | 10/1998 | Saadat |
| 5,833,671 A | 11/1998 | Macoviak et al. |
| 5,833,673 A | 11/1998 | Ockuly et al. |
| 5,834,465 A | 11/1998 | Olney |
| 5,837,003 A | 11/1998 | Ginsburg |
| 5,861,021 A | 1/1999 | Thome et al. |
| 5,868,735 A | 2/1999 | Lafontaine |
| 5,871,526 A | 2/1999 | Gibbs et al. |
| 5,873,835 A | 2/1999 | Hastings et al. |
| 5,879,316 A | 3/1999 | Safar et al. |
| 5,879,329 A | 3/1999 | Ginsburg |
| 5,891,094 A | 4/1999 | Masterson et al. |
| 5,899,898 A | 5/1999 | Arless et al. |
| 5,899,899 A | 5/1999 | Arless et al. |
| 5,902,268 A | 5/1999 | Saab |
| 5,906,588 A | 5/1999 | Safar et al. |
| 5,906,594 A | 5/1999 | Scarfone et al. |
| 5,906,636 A | 5/1999 | Casscells, III et al. |
| 5,910,104 A | 6/1999 | Dobak, III et al. |
| 5,913,856 A | 6/1999 | Chia et al. |
| 5,913,885 A | 6/1999 | Klatz et al. |
| 5,913,886 A | 6/1999 | Soloman |
| 5,916,242 A | 6/1999 | Schwartz |
| 5,957,917 A | 9/1999 | Doiron et al. |
| 5,957,963 A | 9/1999 | Dobak, III |
| 5,964,751 A | 10/1999 | Amplatz et al. |
| 5,967,976 A | 10/1999 | Larsen et al. |
| 5,968,009 A | 10/1999 | Simán |
| 5,971,979 A | 10/1999 | Joye et al. |
| 5,989,238 A | 11/1999 | Ginsburg |
| 6,007,692 A | 12/1999 | Herbert et al. |
| 6,011,995 A | 1/2000 | Guglielmi et al. |
| 6,019,783 A | 2/2000 | Philips et al. |
| 6,024,740 A | 2/2000 | Lesh et al. |
| 6,033,383 A | 3/2000 | Ginsburg |
| 6,042,559 A | 3/2000 | Dobak, III |
| 6,051,019 A | 4/2000 | Dobak, III |
| 6,063,101 A | 5/2000 | Jacobsen et al. |
| 6,096,068 A | 8/2000 | Dobak, III et al. |
| 6,110,168 A | 8/2000 | Ginsburg |
| 6,126,684 A | 10/2000 | Gobin et al. |
| 6,146,411 A | 11/2000 | Noda et al. |
| 6,146,814 A | 11/2000 | Millet |
| 6,149,670 A | 11/2000 | Worthen et al. |
| 6,149,673 A | 11/2000 | Ginsburg |
| 6,149,676 A | 11/2000 | Ginsburg |
| 6,149,677 A | 11/2000 | Dobak, III |
| 6,165,207 A | 12/2000 | Balding et al. |
| 6,182,666 B1 | 2/2001 | Dobak, III |
| 6,194,899 B1 | 2/2001 | Ishihara et al. |
| 6,206,004 B1 | 3/2001 | Schmidt et al. |
| 6,224,624 B1 | 5/2001 | Lasheras et al. |
| 6,231,594 B1 | 5/2001 | Dae |
| 6,231,595 B1 | 5/2001 | Dobak, III |
| 6,235,048 B1 | 5/2001 | Dobak, III |
| 6,238,428 B1 | 5/2001 | Werneth et al. |
| 6,245,095 B1 | 6/2001 | Dobak, III et al. |
| 6,251,129 B1 | 6/2001 | Dobak, III et al. |
| 6,251,130 B1 | 6/2001 | Dobak, III et al. |
| 6,254,626 B1 | 7/2001 | Dobak, III et al. |
| 6,261,312 B1 | 7/2001 | Dobak, III et al. |
| 6,264,679 B1 | 7/2001 | Keller et al. |
| 6,277,143 B1 | 8/2001 | Klatz et al. |
| 6,287,326 B1 | 9/2001 | Pecor |
| 6,290,697 B1 | 9/2001 | Tu et al. |
| 6,290,717 B1 | 9/2001 | Philips |
| 6,295,990 B1 | 10/2001 | Lewis et al. |
| 6,299,599 B1 | 10/2001 | Pham et al. |
| 6,306,161 B1 | 10/2001 | Ginsburg |
| 6,312,452 B1 | 11/2001 | Dobak, III et al. |
| 6,315,754 B1 | 11/2001 | Daoud et al. |
| 6,319,248 B1 | 11/2001 | Nahon |
| 6,325,818 B1 | 12/2001 | Werneth |
| 6,338,727 B1 | 1/2002 | Noda et al. |
| 6,355,029 B1 | 3/2002 | Joye et al. |
| 6,364,899 B1 | 4/2002 | Dobak, III |
| 6,368,304 B1 | 4/2002 | Aliberto et al. |
| 6,379,378 B1 | 4/2002 | Werneth et al. |
| 6,393,320 B2 | 5/2002 | Lasersohn et al. |
| 6,405,080 B1 | 6/2002 | Lasersohn et al. |
| 6,409,747 B1 | 6/2002 | Gobin et al. |
| 6,416,533 B1 | 7/2002 | Gobin et al. |
| 6,419,643 B1 | 7/2002 | Shimada et al. |
| 6,428,563 B1 | 8/2002 | Keller |
| 6,432,102 B2 | 8/2002 | Joye et al. |
| 6,432,124 B1 | 8/2002 | Worthen et al. |
| 6,436,130 B1 | 8/2002 | Philips et al. |
| 6,436,131 B1 | 8/2002 | Ginsburg |
| 6,447,474 B1 | 9/2002 | Balding |
| 6,450,990 B1 | 9/2002 | Walker et al. |
| 6,454,792 B1 | 9/2002 | Noda et al. |
| 6,454,793 B1 | 9/2002 | Evans et al. |
| 6,458,150 B1 | 10/2002 | Evans et al. |

FOREIGN PATENT DOCUMENTS

| | | |
|---|---|---|
| 2001/0001830 A1 | 5/2001 | Dobak, III et al. |
| 2001/0001831 A1 | 5/2001 | Dobak, III et al. |
| 2001/0001832 A1 | 5/2001 | Dobak, III et al. |
| 2001/0002442 A1 | 5/2001 | Dobak, III |
| 2001/0005791 A1 | 6/2001 | Ginsburg |
| 2001/0007951 A1 | 7/2001 | Dobak, III |
| 2001/0008975 A1 | 7/2001 | Dobak, III et al. |
| 2001/0010011 A1 | 7/2001 | Aliberto et al. |

| | | |
|---|---|---|
| 2001/0011184 A1 | 8/2001 | Dobak, III et al. |
| 2001/0011185 A1 | 8/2001 | Dobak, III et al. |
| 2001/0016763 A1 | 8/2001 | Lasheras et al. |
| 2001/0016764 A1 | 8/2001 | Dobak, III |
| 2001/0021865 A1 | 9/2001 | Dobak, III et al. |
| 2001/0021866 A1 | 9/2001 | Dobak, III et al. |
| 2001/0027333 A1 | 10/2001 | Schwartz |
| 2001/0029394 A1 | 10/2001 | Dobak, III et al. |
| 2001/0031946 A1 | 10/2001 | Walker et al. |
| 2001/0032003 A1 | 10/2001 | Pecor |
| 2001/0032004 A1 | 10/2001 | Werneth |
| 2001/0041923 A1 | 11/2001 | Dobak, III |
| 2001/0044644 A1 | 11/2001 | Keller et al. |
| 2001/0047191 A1 | 11/2001 | Lasersohn et al. |
| 2001/0047192 A1 | 11/2001 | Lasersohn et al. |
| 2001/0047196 A1 | 11/2001 | Ginsburg et al. |
| 2001/0049545 A1 | 12/2001 | Lasersohn et al. |
| 2002/0002394 A1 | 1/2002 | Dobak |
| 2002/0007179 A1 | 1/2002 | Dobak et al. |
| 2002/0007202 A1 | 1/2002 | Dobak et al. |
| 2002/0007203 A1 | 1/2002 | Gilmartin et al. |
| 2002/0016621 A1 | 2/2002 | Werneth et al. |
| 2002/0022823 A1 | 2/2002 | Luo et al. |
| 2002/0026227 A1 | 2/2002 | Philips |
| 2002/0029016 A1 | 3/2002 | Pham et al. |
| 2002/0032430 A1 | 3/2002 | Luo et al. |
| 2002/0032474 A1 | 3/2002 | Dobak et al. |
| 2002/0040717 A1 | 4/2002 | Dobak, III |
| 2002/0045852 A1 | 4/2002 | Saab |
| 2002/0045892 A1 | 4/2002 | Kramer |
| 2002/0045925 A1 | 4/2002 | Keller et al. |
| 2002/0049409 A1 | 4/2002 | Noda et al. |
| 2002/0049410 A1 | 4/2002 | Noda et al. |
| 2002/0049484 A1 | 4/2002 | Wernth et al. |
| 2002/0066458 A1 | 6/2002 | Aliberto et al. |
| 2002/0068964 A1 | 6/2002 | Dobak, III |
| 2002/0091378 A1 | 7/2002 | Dobak, III et al. |
| 2002/0091429 A1 | 7/2002 | Dobak, III et al. |
| 2002/0091430 A1 | 7/2002 | Dobak, III et al. |
| 2002/0095200 A1 | 7/2002 | Dobak, III et al. |
| 2002/0095201 A1 | 7/2002 | Worthen et al. |
| 2002/0099427 A1 | 7/2002 | Dobak, III |
| 2002/0103519 A1 | 8/2002 | Dobak, III et al. |
| 2002/0111584 A1 | 8/2002 | Walker et al. |
| 2002/0120314 A1 | 8/2002 | Evans et al. |
| 2002/0128698 A1 | 9/2002 | Dobak, III et al. |
| 2002/0138122 A1 | 9/2002 | Worthen et al. |

FOREIGN PATENT DOCUMENTS

| | | |
|---|---|---|
| AU | 734506 C | 11/2001 |
| AU | 743945 B2 | 2/2002 |
| EP | 0 655 225 A1 | 9/1994 |
| EP | 0 664 990 | 11/1997 |
| EP | 1104273 A1 | 2/2000 |
| EP | 1205167 A2 | 5/2002 |
| EP | 1029520 B1 | 8/2002 |
| FR | 2 447 406 | 1/1980 |
| WO | WO 91/05528 | 5/1991 |
| WO | WO 93/04727 | 3/1993 |
| WO | WO 95/01814 | 1/1995 |
| WO | WO 96/40347 | 12/1996 |
| WO | WO 97/01374 | 1/1997 |
| WO | WO 97/25011 | 7/1997 |
| WO | WO 97/32518 | 9/1997 |
| WO | WO 98/26831 | 6/1998 |
| WO | WO 98/31312 | 7/1998 |
| WO | WO 98/49957 | 11/1998 |
| WO | WO 99/02096 | 1/1999 |
| WO | WO 99/37226 | 7/1999 |
| WO | WO 99/44519 | 9/1999 |
| WO | WO 99/48449 | 9/1999 |
| WO | WO 99/56812 | 11/1999 |
| WO | WO 99/66970 | 12/1999 |
| WO | WO 99/66971 | 12/1999 |
| WO | WO 00/09054 | 2/2000 |
| WO | WO 00/10494 | 3/2000 |
| WO | WO 00/38601 | 7/2000 |
| WO | WO 00/47145 | 7/2000 |
| WO | WO 00/48670 | 8/2000 |
| WO | WO 00/51534 | 9/2000 |
| WO | WO 00/53135 | 9/2000 |
| WO | WO 00/57823 | 10/2000 |
| WO | WO 00/62837 | 10/2000 |
| WO | WO 00/66053 | 11/2000 |
| WO | WO 00/72779 | 12/2000 |
| WO | WO 00/72787 | 12/2000 |
| WO | WO 01/03606 | 1/2001 |
| WO | WO 01/08580 | 2/2001 |
| WO | WO 01/10323 | 2/2001 |
| WO | WO 01/10365 | 2/2001 |
| WO | WO 01/12061 | 2/2001 |
| WO | WO 01/12122 | 2/2001 |
| WO | WO 01/13809 | 3/2001 |
| WO | WO 01/13837 | 3/2001 |
| WO | WO 01/17471 | 3/2001 |
| WO | WO 01/19447 | 3/2001 |
| WO | WO 01/26590 | 4/2001 |
| WO | WO 01/30413 | 4/2001 |
| WO | WO 01/41708 | 6/2001 |
| WO | WO 01/43661 | 6/2001 |
| WO | WO 01/49236 | 7/2001 |
| WO | WO 01/52781 | 7/2001 |
| WO | WO 01/56517 | 8/2001 |
| WO | WO 01/58397 | 8/2001 |
| WO | WO 01/64145 | 9/2001 |
| WO | WO 01/64146 | 9/2001 |
| WO | WO 01/66052 | 9/2001 |

OTHER PUBLICATIONS

Bigelo: Hypothermia, Its Possible Role in Cardiac Surgery; Nov. 1959; pp. 849–866; Annals of Surgery, vol. 132, No. 5.

Cheatle, T.R., et al.; Cryostripping the long and short saphenous veins; Br. J. Surg. 80:1283, 1993.

Dexter: Blood Warms as it Flows Retrograde from a Femoral Cannulation Site to the Carotic Artery During Cardiopulminary Bypass; Nov. 1994; pp. 393–397; Perfusion, vol. 9, No. 6.

Gillinov: Superior Cerebral Protection with Profound Hypothermia During Circulatory Arrest; Nov. 1992; pp. 1432–1439; Ann. Thorac. Surg., vol. 55.

Higazi: The Effect of Ultrasonic Irradiation and Temperature on Fibrinolytic Activity in Vitro; Aug. 1992; pp. 251–253; Thrombosis Research, vol. 69, No. 2.

Imamaki: Retrograde Cerebral Perfusion with Hypothermic Blood Provides Efficient Protection of the Brain; Jul. 1995; pp. 325–333; Journal of Cardiac Surgery, vol. 10, No. 4, Part 1.

Jansen: Near Continuous Cardiac Output by Therodilution; 1997; pp. 233–239; Journal of Clinical Monitoring, vol. 13.

Jolin: Management of a Giant Intracranial Aneurysm Using Surface–Herparinized Extracorporeal Circulation and Controlled Deep Hypothermic Low Flow Perfusion; Jul. 1992; pp. 756–760; Acta Anaesthesiologica Scandanavia.

Kimoto: Open Heart Surgery under Direct Vision with the Aid of Brain–Cooling by Irrigation; Jul. 1995; pp. 592–603; Surgery, vol. 39, No. 4.

Marekovic, Z.: Abstract of Renal Hypothermia in Situ by Venous Passages: Experimental Work on Dogs; 1980; Eur. Urol 6(2); 1 page.

Meden: Effect of Hypothermia and Delayed Thrombolysis in a Rat Embolic Stroke Model; Dec. 1993; pp. 91–98; Acta Neurologica Scandanavia.

Milleret, Rene: La Cryo–chirurgie danes les varices des mimbres inferieurs; Angiologie; Supplemental au No. 110.

Parkins: Brain Cooling in the Prevention of Brain Damage During Periods of Circulatory Occlusion in Dogs: Apr. 1954; pp. 284–289; Animals of Surgery, vol. 140, No. 3.

Piepgras: Rapid Active Internal Core Cooling for Induction of Moderate Hypothermia in Head Injury by Use of an Extracorporeal Heat Exchanger; Feb. 1998; pp. 311–318; Neurosurgery, vol. 42, No. 2.

Rijken: Plasminogen Activation at Low Temperature in Plasma Samples Containing Therapeutic Concentrations of Tissue–Type Plasminogen Activator or Other Thrombolytic Agents: Oct. 1989; pp. 47–52; place of publication unknown.

Schwarta: Cerebral Blood Flow During Low–flow Hypothermic Cardiopulmonary Bypass in Baboons; Jun. 1994; pp. 959–964; Anaesthesiology, vol. 81, No. 4.

Schwartz: Isolated Cerebral Hypothermia by Single Carotid Artery Perfusion of Extracorporeally Cooled Blood in Baboons; 1996; pp. 577–582; Neurosurgery, vol. 39, No. 3.

Schwartz: Selective Cerebral Hypothermia by Means of Transfemoral Internal Carotid Artery Catheterization; May 1996; pp. 571–572; Radiology, vol. 201, No. 2.

Steen: The Detrimental Effects of Prolonged Hypothermia and Rewarming in the Dog; Aug. 1979; pp. 224–231; Anesthesiology, vol. 52, No. 3.

Vandam: Hypothermia; Sep. 1959; pp. 546–553; The New England Journal of Medicine.

White: Cerebral Hypothermia and Circulatory Arrest; Jul. 1978; pp. 450–458; Mayo Clinic Proceedings, vol. 53.

Yenari: Thrombolysis with Tissue Plasminogen Activator (TPA) is Temperature Dependent; Jul. 1994; pp. 475–481; Thrombosis Research, vol. 77, No. 5.

Yoshihara: Changes in Coagulation and Fibrinolysis Occurring in Dogs during Hypothermia; Aug. 1994; pp. 503–512; Thrombosis Research, vol. 37, No. 4.

Zarins: Circulation in Profound Hypothermia; Nov. 1972; pp. 97–104; Journal of Surgical Research, vol. 14, No. 2.

Alfonsi, P., D. I. Sessler, B. Du Manoir, J–C. Levron, J–P. Le Moing, M. Chauvin, The Effects of Meperidine and Sufentanil on the Shivering Threshold in Postoperative Patients, Anesthiology, Jul. 1998, 89(1):43–48.

Benzinger, T.H.; "On Physical Heart Regulation and Sense of Temperature in Man"; Naval Medical Research Institute; Physiology; vol. 45: pp. 645–659; (Feb. 26, 1959).

Brengelmann, George L.; "Specialized Brain Cooling in Humans?"; The FASEB Journal; vol. 7; pp. 1148–1153 (Sep. 1993).

Buggy, D., P. Higgins, C. Moran, F. O'Donovan, and M. McCarroll, Clonidine at Induction Reduces Shivering after General Anaesthesia, 1997, pp. 263–267, Can. J. Anaesth., vol. 44, N. 3.

Cabanac, M.; "Selective Breain Cooling in Humans: fancy or fact?"; The FASEB Journal; vol. 7; pp. 1143–1147 (Sep. 1993).

Cabanac, M; "Selective Brain Cooling and Thermoregulatory Set–Point"; Journal of Basic & Clinical Physiology & Pharmacology; vol. 9; No. 1; pp. 3–13; (1998).

Capogna, G. and D. Celleno, I. V. Clonidine for Post–Extradural Shivering in Parturients: A Preliminary Study, 1993, Brit. Journ. of Anaesth., vol. 71.

Cheng, C. , T. Matsukawa, D. I. Sessler, M. Ozaki, A. Kurz, B. Merrifield, L. Hank, and P. Olofsson, Increasing Mean Skin Temperature Linearly Reduces the Core–Temperature Thresholds for Vasoconstriction and Shivering in Humans, May 1995, pp. 1160–1168, Anesthesiology, vol. 82, N. 5.

Colvett, K. T., A. F. Althausen, B. Bassil, N. M. Heney, F. V. McGovern, H. H. Young, II, D. S. Kaufman, A. L. Zietman, and W. U. Shipley, Opportunities with Combined Modality Therapy for Selective Organ Preservation in Muscle–Invasive Bladder Cancer, 1996, pp. 201–208, Journ. of Surgical Oncology, vol. 63.

Deklunder, G., M. Dauzat, J–L. Lecroart, J–J. Hauser, and Y. Houdas, "Influence of Ventilation of the Face on Thermoregulation in Man during Hyper– and Hypothermia," *Eur. J. Appl. Physiol.,* 1991, 62:342–348.

Gentilello, L. M., "Advances in the Management of Hypothermia," *Horizons in Trauman Surgery,* 75(2): 243–256, Apr. 1995.

Giesbricht, G. G., M. S.. L. Goheen, C. E. Johnston, G. P. Kenny, G. K. Bristow, and J. S. Hayward, Inhibition of Shivering Increases Core Temperature Afterdrop and Attenuates Rewarming in Hypothermic Humans, 1997, 0161–7567:1630–1634, The American Physiological Society.

Giuffre, M., J. Finnie, D. A. Lynam, and D. Smith, *Rewarming Postoperative Patients: Lights, Blankets, or Forced Warm Air,* Dec. 1991, pp. 387–393, Journ. of Post Anaesthesia Nursing, vol. 6, N. 6.

Guffin, A., D. Girard, andJ. A. Kaplan, Shivering Following Cardiac Surgery: Hemodynamic Changes and Reversal, Feb. 1987, pp. 24–28, Journ. of Cardoothoracic Anesthesia, vol. 1, N. 1.

Haley, E. C. et al. "A Randomized Trial of Tirilazad Mesylate in Patients with Acute Stroke (RANTTAS)," *Stroke,* 27(9):1453–1458, 1996.

Iaizzo, Facial Warming Increases the Threshold for Shivering, 1999; pp. 231–239, Journ. of Neurosurgical Anesthesiology, vol. 11, No. 4.

Keegan, M. T. et al. Shivering Complicating the Treatment of Neurologically Impaired Surgical and Intensive Care Unit Patients, Anesthesiology, 91(3):874–876, Sep. 1999,.

Kurz, Martin, et al.; "Naloxone, Meperidine, and Shivering."; *Anesthesiology;* 79(6):1993–1201; Dec. 1993.

Lennon, R. L., M. P. Hosking, M. A. Conover, and W. J. Perkins, Evaluation of a Forced–Air System for Warming Hypothermic Postoperative Patients, 1990, pp. 424–427, Anesth. Analg., vol. 70.

Leslie, K., D. I. Sessler, A. R. Bjorksten, M. Ozaki, T. Matsukawa, and M. Schroeder, Propofol Causes a Dose–Dependent Decrease in the Thermoregulatory Threshold for vasoconstriction but has Little Effect on Sweating, Aug. 1994, pp. 353–360, vol. 81, N. 2.

Maas, C. Intermittent Antegrade Selective Cerebral Perfusion during Circulatory Arrest for Repair of Aortic Arch. Perfusion, vol. 12, No. 2, pp. 127–132, 1997.

Matsukawa, T., A. Kurz, D. I. Sessler, A. R. Bjorksten, B. Merrifield, and C. Cheng, Propofol Linearly Reduces the Vasoconstriction and Shivering Thresholds, May 1995, pp. 1169–1180, Anesthesiology, vol. 82, N. 5.

Meden; The Influence of Body Temperature on Infarct Volume and Thrombolytic Therapy in a Rat Embolic Stroke Model; Feb. 1994; pp. 131–138; Brain Research, vol. 647.

Milleret; Abstract of Cryosclerosis of the Saphenous Veins in Varicose Reflux in the Obese and Elderly; 10.1981; one page; Phlebologie, vol. 34, No. 4.

Pais, S. O., K. D. Tobin, C. B. Austin, and L. Queral, Percutaneous Insertion of the Greenfield Inferior Vena Cava Filter: Experience with Ninety–Six Patients, Oct. 1988, pp. 460–464, Journ. of Vascular Surg., vol. 8, N. 4.

Patton, J. H, T. C. Fabian, M. A. Croce, G. Minard, F. E. Pritchard, and K. A. Kudsk, Prophylactic Greenfield Filters: Acute Complications and Long–Term Follow–Up, Jul. 1996; pp. 231–237; Journal of Trauma: Injury, Infection, and Critical Care, vol. 41, N.2.

Rohrer, M. J. and A. M. Natale, Effect of Hypothermia on the Coagulation Cascade, Oct. 1992, pp. 1402–1405, Critical Care Medicine, vol. 20, N. 10.

Schmid–Elsaesser, R. et al. (1999), Combination Drug Therapy and Mild Hypothermia: A Promising Treatment Strategy for Reversible, Focal Cerebral Ischemia, Stroke, 1891–1899, Jun.

Sessler, Daniel I.; "Mild Perioperative Hypothermia"; The New England Journal of Medicine; 336:1730–1737; Jun. 12, 1997.

Sharkey, A., J. M. Lipton, M. T. Murphy, and A. H. Giesecke, Inhibition of Postanesthestic Shivering with Radiant Heat, Feb. 1987, pp. 249–252, Anesthesiology, vol. 66, N. 2.

Shiraki, K., N. Konda, and S. Sagawa, Esphageal and Tympanic Temperature Responses to Core Blood Temperature Changes during Hyperthermia, *J. Appl. Physiol. 61(1):98–102* (1986).

Simon, M., C. A. Athanasoulis, D. Kim, F. L. Steinberg, D. H Porter, B. H. Byse, S. Kleshinski, S. Geller, D. E. Orron, and A. C. Waltman; Simon Nitinol Inferior Vena Cava Filter: Initial Clinical Experience, Jul. 1989, pp. 99–103; Radiology.

Villamaria, F. J., C. E. Baisden, A. Hillis, M. H. Rajab, and P. A. Rinaldi, "Forced–Air Warming is No More Effective than Conventional Methods for Raising Postoperative Core Temperature After Cardiac Surgery," *Journ. Cardiothoracic and Vascular Anesth., 11(6):708–711,* Oct. 1997.

Zweifler, R. M. and D. I. Sessler, "Thermoregulatory Vasoconstriction and Shivering Impede Therapeutic Hypothermia in Acute Ischemic Stroke Patients," *Journ. Stroke and Cerebrovascular Diseases,* 6(2):100–104, 1996.

* cited by examiner

LUMEN DESIGN FOR CATHETER

CROSS-REFERENCE TO RELATED APPLICATION

This is a divisional of application Ser. No. 09/519,022 filed on Mar. 3, 2000, now 6,379,378.

BACKGROUND OF THE INVENTION

1. Field of the Invention

The present invention relates generally to lumen designs for catheters. More particularly, the invention relates to lumen designs for catheters that modify and control the temperature of a selected body organ.

2. Background Information

Organs in the human body, such as the brain, kidney and heart, are maintained at a constant temperature of approximately 37° C. Hypothermia can be clinically defined as a core body temperature of 35° C. or less. Hypothermia is sometimes characterized further according to its severity. A body core temperature in the range of 33° C. to 35° C. is described as mild hypothermia. A body temperature of 28° C. to 32° C. is described as moderate hypothermia. A body core temperature in the range of 24° C. is described as severe hypothermia.

Hypothermia is uniquely effective in reducing brain injury caused by a variety of neurological insults and may eventually play an important role in emergency brain resuscitation. Experimental evidence has demonstrated that cerebral cooling improves outcome after global ischemia, focal ischemia, or traumatic brain injury. For this reason, hypothermia may be induced in order to reduce the effect of certain bodily injuries to the brain as well as other organs.

Cerebral hypothermia has traditionally been accomplished through whole body cooling to create a condition of total body hypothermia in the range of 20° C. to 30° C.

Catheters have been developed which are inserted into the bloodstream of the patient in order to induce total body hypothermia. For example, U.S. Pat. No. 3,425,419 to Dato describes a method and apparatus of lowering and raising the temperature of the human body. Dato induces moderate hypothermia in a patient using a metallic catheter. The metallic catheter has an inner passageway through which a fluid, such as water, can be circulated. The catheter is inserted through the femoral vein and then through the inferior vena cava as far as the right atrium and the superior vena cava. The Dato catheter has an elongated cylindrical shape and is constructed from stainless steel. By way of example, Dato suggests the use of a catheter approximately 70 cm in length and approximately 6 mm in diameter.

Due to certain problems sometimes associated with total body hypothermia, attempts have been made to provide more selective cooling. For example, cooling helmets or headgear have been used in an attempt to cool only the head rather than the patient's entire body. However, such methods rely on conductive heat transfer through the skull and into the brain. One drawback of using conductive heat transfer is that the process of reducing the temperature of the brain is prolonged. Also, it is difficult to precisely control the temperature of the brain when using conduction due to the temperature gradient that must be established externally in order to sufficiently lower the internal temperature. In addition, when using conduction to cool the brain, the face of the patient is also subjected to severe hypothermia, increasing discomfort and the likelihood of negative side effects. It is known that profound cooling of the face can cause similar cardiovascular side effects as total body cooling. From a practical standpoint, such devices are cumbersome and may make continued treatment of the patient difficult or impossible.

Selected organ hypothermia has been accomplished using extracorporeal perfusion, as detailed by Arthur E. Schwartz, M.D. et al., in *Isolated Cerebral Hypothermia by Single Carotid Artery Perfusion of Extracorporeally Cooled Blood in Baboons,* which appeared in Vol. 39, No. 3, NEUROSURGERY 577 (September, 1996). In this study, blood was continually withdrawn from baboons through the femoral artery. The blood was cooled by a water bath and then infused through a common carotid artery with its external branches occluded. Using this method, normal heart rhythm, systemic arterial blood pressure and arterial blood gas values were maintained during the hypothermia. This study showed that the brain could be selectively cooled to temperatures of 20° C. without reducing the temperature of the entire body. However, external circulation of blood is not a practical approach for treating humans because the risk of infection, need for anticoagulation, and risk of bleeding is too great. Further, this method requires cannulation of two vessels making it more cumbersome to perform particularly in emergency settings. Even more, percutaneous cannulation of the carotid artery is difficult and potentially fatal due to the associated arterial wall trauma. Finally, this method would be ineffective to cool other organs, such as the kidneys, because the feeding arteries cannot be directly cannulated percutaneously.

Selective organ hypothermia has also been attempted by perfusion of a cold solution such as saline or perflourocarbons. This process is commonly used to protect the heart during heart surgery and is referred to as cardioplegia. Perfusion of a cold solution has a number of drawbacks, including a limited time of administration due to excessive volume accumulation, cost, and inconvenience of maintaining the perfusate and lack of effectiveness due to the temperature dilution from the blood. Temperature dilution by the blood is a particular problem in high blood flow organs such as the brain.

Catheters adapted for delivering heat transfer fluids at temperatures above or below normal body temperatures to selected internal body sites have been devised in the past (See, for example, U.S. Pat. No. 5,624,392 to Saab). These catheters often have a concentric, coaxial configuration of multiple lumens. The configurations often have a first central lumen adapted to receive a guide surrounded by a concentric second supply lumen adapted to supply a working fluid to a distal portion of the catheter and an outer concentric third return lumen, which surrounds the second lumen, adapted to return a working fluid to a fluid source. A problem with this configuration is that the working fluid in the supply lumen makes surface area contact with both an outer wall, which partially defines the outer limits of the second lumen, and an inner wall, which defines the first lumen, leading to increased heat transfer between the walls and the working fluid. Thus, if the second supply lumen in the catheter is designed to deliver a cooling fluid to the distal portion of the catheter, the increased surface area contact caused by this configuration unnecessarily warms the cooling fluid prior to delivery to the distal portion of the catheter. Another problem with these catheters is that the supply lumen(s) and return lumen(s) are not sized relative to each other to maximize the flow rate through the catheter. Hence, they do not optimize heating and/or cooling catheter performance.

BRIEF SUMMARY OF THE INVENTION

The present invention involves a device for heating or cooling a surrounding fluid in a blood vessel that addresses and solves the problems discussed above with multiple lumen arrangements of catheters in the past. The device includes an elongated catheter body, a heat transfer element located at a distal portion of the catheter body and including an interior, an elongated supply lumen adapted to deliver a working fluid to the interior of the heat transfer element and having a hydraulic diameter, an elongated return lumen adapted to return a working fluid from the interior of the heat transfer element and having a hydraulic diameter, and wherein the ratio of the hydraulic diameter of the return lumen to the hydraulic diameter of the supply lumen is substantially equal to 0.75.

Implementations of the above aspect of the invention may include one or more of the following. The supply lumen may be disposed substantially within the return lumen. One of the supply lumen and return lumen may have a cross-sectional shape that is substantially luniform. One of the supply lumen and the return lumen has a cross-sectional shape that is substantially annular. The supply lumen has a general cross-sectional shape and the return lumen has a general cross-sectional shape different from the general cross-sectional shape of the supply lumen. The catheter assembly includes an integrated elongated bi-lumen member having a first lumen adapted to receive a guide wire and a second lumen comprising either the supply lumen or the return lumen. The bi-lumen member has a cross-sectional shape that is substantially in the shape of a figure eight. The first lumen has a cross-sectional shape that is substantially circular and the second lumen has a cross-sectional shape that is substantially annular. The heat transfer element includes means for inducing mixing in a surrounding fluid. The device further includes means for inducing wall jets or means for further enhancing mixing of the working fluid to effect further heat transfer between the heat transfer element and working fluid. The heat transfer element includes an interior distal portion and the supply lumen includes first means for delivering working fluid to the interior distal portion of the heat transfer element and second means for delivering working fluid to the interior of the heat transfer element at one or more points point proximal to the distal portion of the heat transfer element.

A second aspect of the invention involves a catheter assembly capable of insertion into a selected blood vessel in the vascular system of a patient. The catheter assembly includes an elongated catheter body including an operative element having an interior at a distal portion of the catheter body, an elongated supply lumen adapted to deliver a working fluid to the interior of the distal portion and having a hydraulic diameter, an elongated return lumen adapted to return a working fluid from the interior of the operative element and having a hydraulic diameter, and wherein the ratio of the hydraulic diameter of the return lumen to the hydraulic diameter of the supply lumen being substantially equal to 0.75.

Any of the implementations described above with respect to the first aspect of the invention also apply to the second aspect of the invention. Further, implementations of the second aspect of the invention may include one or more of the following. The operative element may include a heat transfer element adapted to transfer heat to or from the working fluid. The heat transfer element may include means for inducing mixing in a surrounding fluid. The operative element may include a catheter balloon adapted to be inflated with the working fluid.

A third aspect of the invention involves a device for heating or cooling a surrounding fluid in a vascular blood vessel. The device includes an elongated catheter body, a heat transfer element located at a distal portion of the catheter body and including an interior, an integrated elongated bi-lumen member located within the catheter body and including a first lumen adapted to receive a guide wire and a second lumen, the second lumen comprising either a supply lumen to deliver a working fluid to an interior of the heat transfer element or a return lumen to return a working fluid from the interior of the heat transfer element, and a third lumen comprising either a supply lumen to deliver a working fluid to an interior of the heat transfer element or a return lumen to return a working fluid from the interior of the heat transfer element.

Implementations of the third aspect of the invention may include one or more of the following. The catheter body includes an internal wall and the integrated bi-lumen member includes an exterior wall, and the third lumen is substantially defined by the internal wall of the catheter body and the exterior wall of the bi-lumen member. Both the catheter body and the bi-lumen member are extruded. The bi-lumen member is disposed substantially within the third lumen. The second lumen has a cross-sectional shape that is substantially luniform. The third lumen has a cross-sectional shape that is substantially annular. The second lumen has a general cross-sectional shape and the third lumen has a general cross-sectional shape different from the general cross-sectional shape of the second lumen. The bi-lumen member has a cross-sectional shape that is substantially in the shape of a figure eight. The first lumen has a cross-sectional shape that is substantially circular and the second lumen has a cross-sectional shape that is substantially luniform. The heat transfer element includes means for inducing mixing in a surrounding fluid. The device further includes means for inducing wall jets or means for further enhancing mixing of the working fluid to effect further heat transfer between the heat transfer element and working fluid. The heat transfer element includes an interior distal portion and the supply lumen includes first means for delivering working fluid to the interior distal portion of the heat transfer element and second means for delivering working fluid to the interior of the heat transfer element at one or more points point proximal to the distal portion of the heat transfer element.

A fourth aspect of the present invention involves a catheter assembly capable of insertion into a selected blood vessel in the vascular system of a patient. The catheter assembly includes an elongated catheter body including an operative element having an interior at a distal portion of the catheter body, an integrated elongated bi-lumen member located within the catheter body and including a first lumen adapted to receive a guide wire and a second lumen, the second lumen comprising either a supply lumen to deliver a working fluid to the interior of the operative element or a return lumen to return a working fluid from the interior of the operative element, and a third lumen within the catheter body and comprising either a supply lumen to deliver a working fluid to an interior of the operative element or a return lumen to return a working fluid from the interior of the operative element.

Any of the implementations described above with respect to the third aspect of the invention also apply to the fourth aspect of the invention.

A fifth aspect of the invention involves a method of manufacturing a catheter assembly for heating or cooling a surrounding fluid in a blood vessel. The method involves extruding an elongated catheter body; locating a heat transfer element including an interior at a distal portion of the catheter body; extruding an integrated elongated bi-lumen member including a first lumen adapted to receive a guide wire and a second lumen, the second lumen comprising either a supply lumen to deliver a working fluid to an interior of the heat transfer element or a return lumen to return a working fluid from the interior of the heat transfer element; and providing the integrated bi-lumen member substantially within the elongated catheter body so that a third lumen is formed, the third lumen comprising either a supply lumen to deliver a working fluid to an interior of the heat transfer element or a return lumen to return a working fluid from the interior of the heat transfer element.

Implementations of the fifth aspect of the invention may include one or more of the following. The second lumen has a hydraulic diameter and the third lumen has a hydraulic diameter, and the ratio of the hydraulic diameter of the second lumen to the hydraulic diameter of the third lumen is substantially equal to 0.75. The step of providing the integrated bi-lumen member substantially within the elongated catheter body includes simultaneously extruding the integrated bi-lumen member substantially within the elongated catheter body.

A sixth aspect of the present invention involves a method of manufacturing a catheter assembly. The method includes extruding an elongated catheter body; locating an operative element including an interior at a distal portion of the catheter body; extruding an integrated elongated bi-lumen member including a first lumen adapted to receive a guide wire and a second lumen, the second lumen comprising either a supply lumen to deliver a working fluid to an interior of the operative element or a return lumen to return a working fluid from the interior of the operative element; and providing the integrated bi-lumen member substantially within the elongated catheter body so that a third lumen is formed, the third lumen comprising either a supply lumen to deliver a working fluid to an interior of the operative element or a return lumen to return a working fluid from the interior of the operative element.

Any of the implementations described above with respect to the fifth aspect of the invention also apply to the sixth aspect of the invention.

A seventh aspect of the present invention involves a device for heating or cooling a surrounding fluid in a blood vessel. The device includes an elongated catheter body, a heat transfer element located at a distal portion of the catheter body and including an interior distal portion and an interior portion defining at least a first heat transfer segment and a second heat transfer segment, and at least one elongated supply lumen located within the catheter body, the at least one elongated supply lumen including first means for delivering working fluid to the interior distal portion of the first heat transfer segment and second means for delivering working fluid to the interior portion of the second heat transfer segment.

In an implementation of the seventh aspect of the invention, the second working fluid delivering means is adapted to deliver working fluid to the interior portion of the heat transfer element near a midpoint of the heat transfer element.

An eighth aspect of the present invention involves a device for heating or cooling a surrounding fluid in a blood vessel. The device includes an elongated catheter body, a heat transfer element located at a distal portion of the catheter body and including an interior distal portion and an interior portion, and at least one elongated supply lumen located within the catheter body, the at least one elongated supply lumen including first means for delivering working fluid to the interior distal portion of the heat transfer element and second means for delivering working fluid to the interior portion of the heat transfer element at one or more points proximal to the distal portion of the heat transfer element.

In an implementation of the eighth aspect of the invention, the second working fluid delivering means is adapted to deliver working fluid to the interior portion of the heat transfer element near a midpoint of the heat transfer element.

A ninth aspect of the present invention involves a device for heating or cooling a surrounding fluid in a blood vessel. The device includes an elongated catheter body, a heat transfer element located at a distal portion of the catheter body and including an interior distal portion and an interior portion defining at least a first heat transfer segment and a second heat transfer segment, a first elongated supply lumen located within the catheter body and terminating at the interior distal portion of the heat transfer element into first means for delivering working fluid to the interior distal portion of the heat transfer element, and a second elongated supply lumen located within the catheter body and terminating at a point proximal to the distal portion of the heat transfer element into second means for delivering working fluid to the interior portion of the heat transfer element at a point proximal to the distal portion of the heat transfer element.

In an implementation of the ninth aspect of the invention, the second working fluid delivering means is adapted to deliver working fluid to the interior portion of the heat transfer element near a midpoint of the heat transfer element.

A tenth aspect of the present invention involves a device for heating or cooling a surrounding fluid in a blood vessel. The device includes an elongated catheter body, a heat transfer element located at a distal portion of the catheter body and including an interior distal portion and an interior portion defining at least a first heat transfer segment interior portion and a second heat transfer segment interior portion, a first elongated supply lumen located within the catheter body and terminating at the interior distal portion of the first heat transfer segment into first means for delivering working fluid to the interior of the first heat transfer segment, and a second elongated supply lumen located within the catheter body and terminating at a point proximal to the distal portion of the heat transfer element into second means for delivering working fluid to the interior portion of the second heat transfer segment.

In an implementation of the tenth aspect of the invention, the second working fluid delivering means is adapted to deliver working fluid to the interior portion of the heat transfer element near a midpoint of the heat transfer element.

An eleventh aspect of the present invention involves a device for heating or cooling a surrounding fluid in a blood vessel. The device includes an elongated catheter body, a heat transfer element located at a distal portion of the catheter body and including an interior portion adapted to induce mixing of a working fluid to effect heat transfer between the heat transfer element and working fluid, the heat transfer element including at least a first heat transfer segment, a second heat transfer segment, and an intermediate segment between the first heat transfer segment and the second heat transfer segment, an elongated supply lumen member located within the catheter body and adapted to deliver the working fluid to the interior of the heat transfer element, the supply lumen member including a circular outer surface, an elongated return lumen defined in part by the outer surface of the supply lumen member and the interior portion of the heat transfer element and adapted to return the working fluid from the interior of the heat transfer element, and wherein the distance between the interior portion of the heat transfer element and the outer surface of the supply lumen member adjacent the intermediate segment is less than the distance between the interior portion of the heat transfer element and the outer surface of the supply lumen member adjacent the first heat transfer segment.

Implementations of the eleventh aspect of the invention may include one or more of the following. The distance between the interior portion of the heat transfer element and the outer surface of the supply lumen member adjacent the intermediate segment is such that the characteristic flow resulting from a flow of working fluid is at least of a transitional nature. The intermediate segment includes an interior diameter that is less than the interior diameter of the first heat transfer segment or the second heat transfer segment. The supply lumen member includes an outer diameter adjacent the intermediate segment that is greater than its outer diameter adjacent the first heat transfer segment or the second heat transfer segment. The supply lumen member comprises a multiple-lumen member. The supply lumen member includes a supply lumen having a hydraulic diameter and the return lumen has a hydraulic diameter substantially equal to 0.75 the hydraulic diameter of the supply lumen. The intermediate segment includes a flexible bellows joint.

A twelfth aspect of the present invention involves a device for heating or cooling a surrounding fluid in a blood vessel. The device includes an elongated catheter body, a heat transfer element located at a distal portion of the catheter body and including an interior portion adapted to induce mixing of a working fluid to effect heat transfer between the heat transfer element and working fluid, an elongated supply lumen member located within the catheter body and adapted to deliver the working fluid to the interior of the heat transfer element, an elongated return lumen member located within the catheter body and adapted to return the working fluid from the interior of the heat transfer element, and means located within the heat transfer element for further enhancing mixing of the working fluid to effect further heat transfer between the heat transfer element and working fluid.

Implementations of the twelfth aspect of the invention may include one or more of the following. The supply lumen member comprises a multiple-lumen member having a circular outer surface. The supply lumen member includes a supply lumen having a hydraulic diameter and the return lumen has a hydraulic diameter substantially equal to 0.75 of the hydraulic diameter of the supply lumen.

A thirteenth aspect of the present invention involves a device for heating or cooling a surrounding fluid in a blood vessel. The device includes an elongated catheter body, a heat transfer element located at a distal portion of the catheter body and including an interior portion adapted to induce mixing of a working fluid to effect heat transfer between the heat transfer element and working fluid, an elongated supply lumen member located within the catheter body and adapted to deliver the working fluid to the interior of the heat transfer element, an elongated return lumen member located within the catheter body and adapted to return the working fluid from the interior of the heat transfer element, and a mixing-enhancing mechanism located within the heat transfer element and adapted to further mix the working fluid to effect further heat transfer between the heat transfer element and working fluid.

Implementations of the thirteenth aspect of the invention may include one or more of the following. The supply lumen member comprises a multiple-lumen member having a circular outer surface. The supply lumen member includes a supply lumen having a hydraulic diameter and the return lumen has a hydraulic diameter substantially equal to the hydraulic diameter of the supply lumen.

A fourteenth aspect of the present invention involves a method of heating or cooling a surrounding fluid in a blood vessel. The method includes providing a device for heating or cooling a surrounding fluid in a blood vessel within the blood stream of a blood vessel, the device including an elongated catheter body, a heat transfer element located at a distal portion of the catheter body and including an interior portion adapted to induce mixing of a working fluid to effect heat transfer between the heat transfer element and working fluid, an elongated supply lumen member located within the catheter body and adapted to deliver the working fluid to the interior of the heat transfer element, an elongated return lumen member located within the catheter body and adapted to return the working fluid from the interior of the heat transfer element, and a mixing-enhancing mechanism located within the heat transfer element and adapted to further mix the working fluid to effect further heat transfer between the heat transfer element and working fluid; causing a working fluid to flow to and along the interior portion of the heat transfer element of the device using the supply lumen and return lumen; facilitating the transfer of heat between the working fluid and the heat transfer element by effecting mixing of the working fluid with the interior portion adapted to induce mixing of a working fluid; facilitating additional transfer of heat between the working fluid and the heat transfer element by effecting further mixing of the working fluid with the interior portion with the mixing-enhancing mechanism; causing heat to be transferred between the blood stream and the heat transfer element by the heat transferred between the heat transfer element and working fluid.

The novel features of this invention, as well as the invention itself, will be best understood from the attached drawings, taken along with the following description, in which similar reference characters refer to similar parts, and in which:

DETAILED DESCRIPTION OF THE INVENTION

Figure 1:
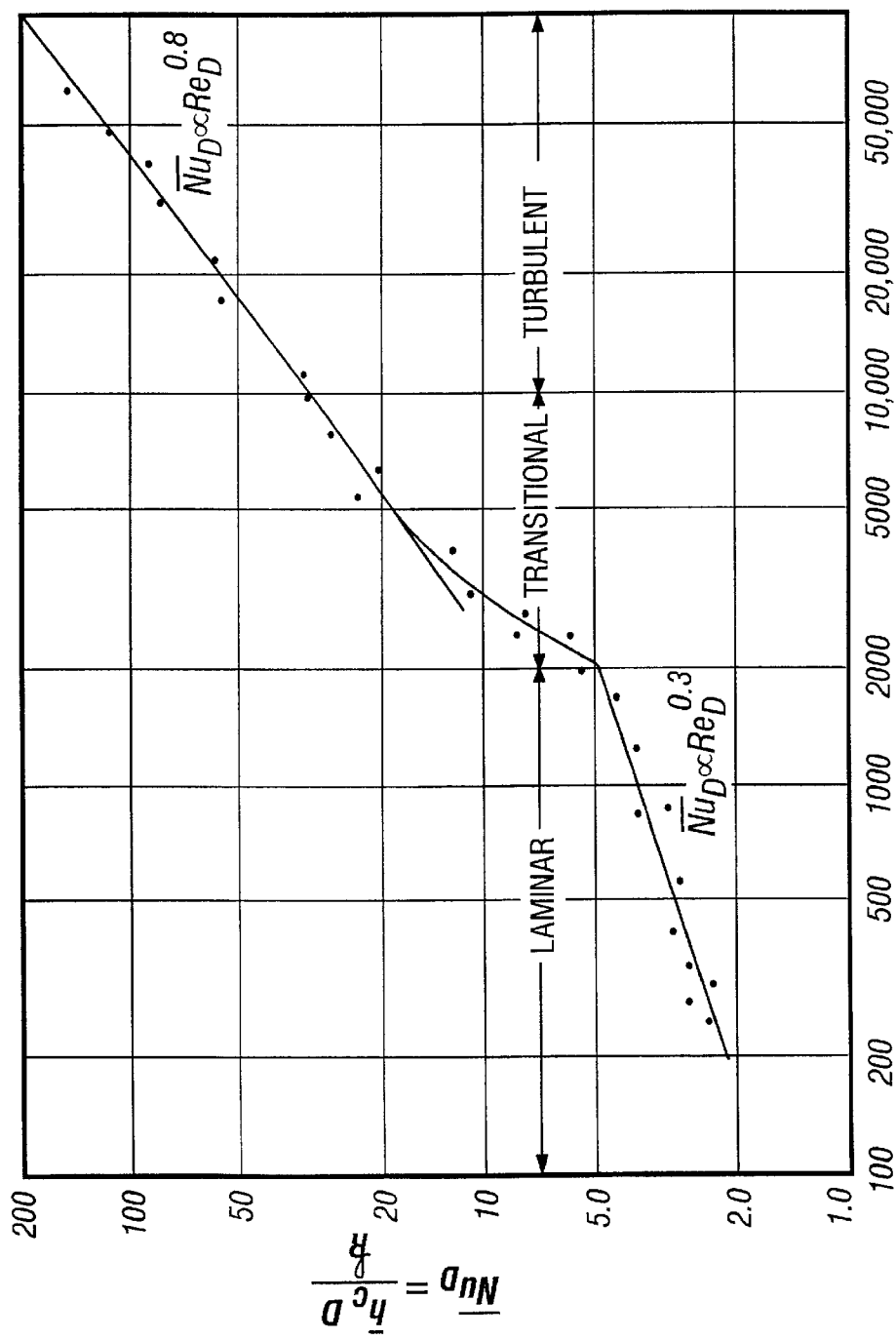
FIG. 1 is a graph showing the relationship between the Nusselt number (Nu) and the Reynolds number (Re) for air flowing through a long heated pipe at uniform wall temperature.

The temperature of a selected organ may be intravascularly regulated by a heat transfer element placed in the organ's feeding artery to absorb or deliver heat to or from the blood flowing into the organ. While the method is described with respect to blood flow into an organ, it is understood that heat transfer within a volume of tissue is analogous. In the latter case, heat transfer is predominantly by conduction.

The heat transfer may cause either a cooling or a heating of the selected organ. A heat transfer element that selectively alters the temperature of an organ should be capable of providing the necessary heat transfer rate to produce the desired cooling or heating effect within the organ to achieve a desired temperature. If placed in the venous system, whole body cooling may also be effected.

On the arterial side, the heat transfer element should be small and flexible enough to fit within the feeding artery while still allowing a sufficient blood flow to reach the organ in order to avoid ischemic organ damage. Feeding arteries, like the carotid artery, branch off the aorta at various levels. Subsidiary arteries continue to branch off these initial branches. For example, the internal carotid artery branches off the common carotid artery near the angle of the jaw. The heat transfer element is typically inserted into a peripheral artery, such as the femoral artery, using a guide catheter or guide wire, and accesses a feeding artery by initially passing though a series of one or more of these branches. Thus, the flexibility and size, e.g., the diameter, of the heat transfer element are important characteristics. This flexibility is achieved as is described in more detail below.

These points are illustrated using brain cooling as an example. Other organs, as well as the whole body, may also be cooled. The common carotid artery supplies blood to the head and brain. The internal carotid artery branches off the common carotid artery to supply blood to the anterior cerebrum. The heat transfer element may be placed into the common carotid artery or into both the common carotid artery and the internal carotid artery.

The benefits of hypothermia described above are achieved when the temperature of the blood flowing to the brain is reduced to between 30° C. and 32° C. A typical brain has a blood flow rate through each carotid artery (right and left) of approximately 250–375 cubic centimeters per minute (cc/min). With this flow rate, calculations show that the heat transfer element should absorb approximately 75–175 watts of heat when placed in one of the carotid arteries to induce the desired cooling effect. Smaller organs may have less blood flow in their respective supply arteries and may require less heat transfer, such as about 25 watts.

The method employs conductive and convective heat transfers. Once the materials for the device and a working fluid are chosen, the conductive heat transfers are solely dependent on the temperature gradients. Convective heat transfers, by contrast, also rely on the movement of fluid to transfer heat. Forced convection results when the heat transfer surface is in contact with a fluid whose motion is induced (or forced) by a pressure gradient, area variation, or other such cause. In the case of arterial flow, the beating heart provides an oscillatory pressure gradient to force the motion of the blood in contact with the heat transfer surface. One of the aspects of the device uses turbulence to enhance this forced convective heat transfer.

The rate of convective heat transfer Q is proportional to the product of S, the area of the heat transfer element in direct contact with the fluid, $\Delta T = T_b - T_s$, the temperature differential between the surface temperature $T_s$ of the heat transfer element and the free stream blood temperature $T_b$, and $\overline{h}_c$, the average convection heat transfer coefficient over the heat transfer area. $\overline{h}_c$ is sometimes called the "surface coefficient of heat transfer" or the "convection heat transfer coefficient".

The magnitude of the heat transfer rate Q to or from the fluid flow can be increased through manipulation of the above three parameters. Practical constraints limit the value of these parameters and how much they can be manipulated. For example, the internal diameter of the common carotid artery ranges from 6 to 8 mm. Thus, the heat transfer element residing therein may not be much larger than 4 mm in diameter to avoid occluding the vessel. The length of the heat transfer element should also be limited. For placement within the internal and common carotid artery, the length of the heat transfer element is limited to about 10 cm. This estimate is based on the length of the common carotid artery, which ranges from 8 to 12 cm.

Consequently, the value of the surface area S is limited by the physical constraints imposed by the size of the artery into which the device is placed. Surface features can be used to increase the surface area of the heat transfer element; however, these features alone generally cannot provide enough surface area enhancement to meet the required heat transfer rate to effectively cool the brain.

One may also attempt to vary the magnitude of the heat transfer rate by varying $\Delta T$. The value of $\Delta T = T_b - T_s$ can be varied by varying the surface temperature $T_s$ of the heat transfer element. The allowable surface temperature of the heat transfer element is limited by the characteristics of blood. The blood temperature is fixed at about 37° C., and blood freezes at approximately 0° C. When the blood approaches freezing, ice emboli may form in the blood which may lodge downstream, causing serious ischemic injury. Furthermore, reducing the temperature of the blood also increases its viscosity which results in a small decrease in the value of $\overline{h}_c$. Increased viscosity of the blood may further result in an increase in the pressure drop within the artery, thus compromising the flow of blood to the brain. Given the above constraints, it is advantageous to limit the surface temperature of the heat transfer element to approximately 1° C.–5° C., thus resulting in a maximum temperature differential between the blood stream and the heat transfer element of approximately 32° C.–36° C.

One may also attempt to vary the magnitude of the heat transfer rate by varying $\overline{h}_c$. Fewer constraints are imposed on the value of the convection heat transfer coefficient $\overline{h}_c$. The mechanisms by which the value of $\overline{h}_c$ may be increased are complex. However, one way to increase $\overline{h}_c$ for a fixed mean value of the velocity is to increase the level of turbulent kinetic energy in the fluid flow.

The heat transfer rate $Q_{no-flow}$ in the absence of fluid flow is proportional to $\Delta T$, the temperature differential between the surface temperature $T_s$ of the heat transfer element and the free stream blood temperature $T_b$ times k, the diffusion constant, and is inversely proportion to distance D across which heat is being transferred.

The magnitude of the enhancement in heat transfer by fluid flow can be estimated by taking the ratio of the heat transfer rate with fluid flow to the heat transfer rate in the absence of fluid flow $N = Q_{flow}/Q_{no-flow} = \overline{h}_c/(k/\delta)$. This ratio is called the Nusselt number ("Nu"). For convective heat transfer between blood and the surface of the heat transfer element, Nusselt numbers of 50–80 have been found to be appropriate for selective cooling applications of various organs in the human body. Nusselt numbers are generally dependent on several other numbers: the Reynolds number, the Womersley number, and the Prandtl number.

For example, FIG. 1 illustrates the dependency of the Nusselt number on the Reynolds number for a fluid flowing through a long duct, i.e., air flowing though a long heated pipe at a uniform wall temperature. Although FIG. 1 illustrates this relationship for a different fluid through a different structure, the inventors of the present invention believe a similar relationship exists for blood flow through a blood vessel. FIG. 1 illustrates that flow is laminar when the Reynolds number is below some number, in this case about 2100. In the range of Reynolds numbers between another set of numbers, in this case 2100 and 10,000, a transition from laminar to turbulent flow takes place. The flow in this regime is called transitional. The mixing caused by the heat transfer element of the present invention produces a flow that is at least transitional. At another Reynolds number, in the case above, about 10,000, the flow becomes fully turbulent.

The type of flow that occurs is important because in laminar flow through a duct, there is no mixing of warmer and colder fluid particles by eddy motion. Thus, the only heat transfer that takes place is through conduction. Since most fluids have small thermal conductivities, the heat transfer coefficients in laminar flow are relatively small. In transitional and turbulent flow, mixing occurs through eddies that carry warmer fluid into cooler regions and vice versa. Since the mixing motion, even if it is only on a small scale compared to fully turbulent flow, accelerates the transfer of heat considerably, a marked increase in the heat transfer coefficient occurs above a certain Reynolds number, which in the graph of FIG. 1 is about 2100. It can be seen from FIG. 1 that it is at approximately this point where the Nusselt number increases more dramatically. A different set of numbers may be measured for blood flow through an artery or vein. However, the inventors believe that a Nusselt number at least in the transitional region is important for enhanced heat transfer.

Stirring-type mechanisms, which abruptly change the direction of velocity vectors, may be utilized to induce at least transitional flow, increasing the heat transfer rate by this eddy creation. The level of turbulence or mixing so created is characterized by the turbulence intensity $\theta$. Turbulence intensity $\theta$ is defined as the root mean square of the fluctuating velocity divided by the mean velocity. Such mechanisms can create high levels of turbulence intensity in the free stream, thereby increasing the heat transfer rate. This turbulence intensity should ideally be sustained for a significant portion of the cardiac cycle, and should ideally be created throughout the free stream and not just in the boundary layer.

Turbulence does occur for a short period in the cardiac cycle anyway. In particular, the blood flow is turbulent during a small portion of the descending systolic flow. This portion is less than 20% of the period of the cardiac cycle. If a heat transfer element is placed co-axially inside an artery, the heat transfer rate will be enhanced during this short interval. For typical of these fluctuations, the turbulence intensity is at least 0.05. In other words, the instantaneous velocity fluctuations deviate from the mean velocity by at least 5%. In some embodiments, lower fluctuations may be employed, such as 3% or even 2%. Although ideally turbulence is created throughout the entire period of the cardiac cycle, the benefits of turbulence are obtained if the turbulence or mixing is sustained for 75%, 50% or even as low as 30% or 20% of the cardiac cycle. Of course, such turbulence or mixing is much less, or is even nonexistent, in veins or in very small arteries.

One type of mixing-inducing heat transfer element which may be advantageously employed is a heat transfer element made of a high thermal conductivity material, such as metal. The use of a high thermal conductivity material increases the heat transfer rate for a given temperature differential between the coolant within the heat transfer element and the blood. This facilitates the use of a higher temperature coolant within the heat transfer element, allowing safer coolants, such as water, to be used. Highly thermally conductive materials, such as metals, tend to be rigid. Bellows provided a high degree of articulation that compensated for the intrinsic stiffness of the metal. In another embodiment, the bellows may be replaced with a straight metal tube having a predetermined thickness to allow flexibility via bending of the metal. Alternatively, the bellows may be replaced with a polymer tube, e.g., a latex rubber tube, a plastic tube, or a flexible plastic corrugated tube.

The device size may be minimized, e.g., less than 4 mm, to prevent blockage of the blood flowing in the vessel. The design of the heat transfer element should facilitate flexibility in an inherently inflexible material.

Figure 2:
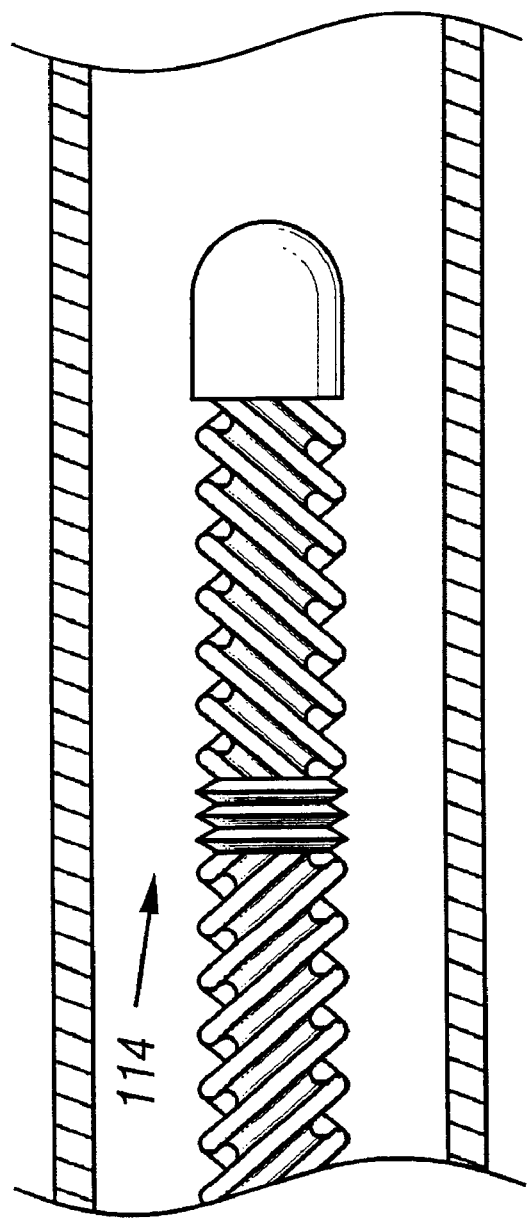
FIG. 2 is a front view of a first embodiment of a mixing-inducing heat transfer element according to the principles of the invention within an artery.

To create the desired level of turbulence intensity in the blood free stream during the whole cardiac cycle, one embodiment of the device uses a modular design. This design creates helical blood flow and produces a high level of mixing in the free stream by periodically forcing abrupt changes in the direction of the helical blood flow. FIG. 2 is a perspective view of such a mixing-inducing heat transfer element within an artery. Transitional to turbulent flow would be found at point 114, in the free stream area. The abrupt changes in flow direction are achieved through the use of a series of two or more heat transfer segments, each comprised of one or more helical ridges.

The use of periodic abrupt changes in the helical direction of the blood flow in order to induce strong free stream turbulence or mixing may be illustrated with reference to a common clothes washing machine. The rotor of a washing machine spins initially in one direction causing laminar flow. When the rotor abruptly reverses direction, significant mixing is created within the entire wash basin as the changing currents cause random turbulent motion within the clothes-water slurry.

Figure 3:
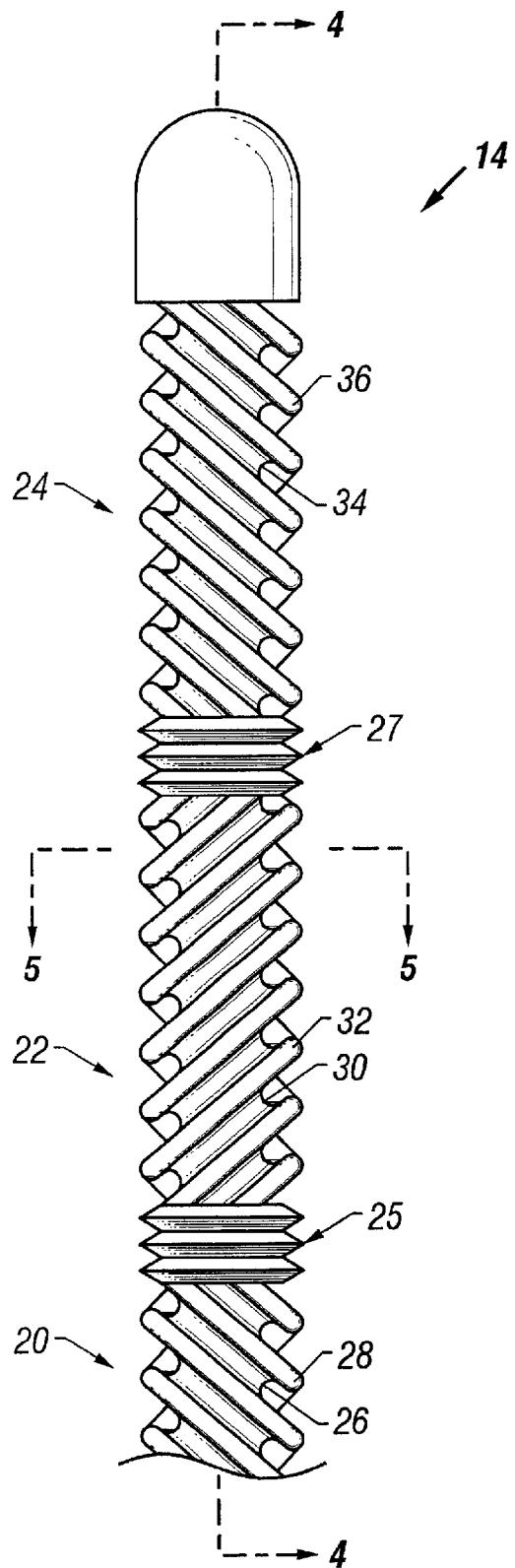
FIG. 3 is a more detailed front view of the heat transfer element of FIG. 1.

FIG. 3 is an elevation view of one embodiment of a heat transfer element 14. The heat transfer element 14 is comprised of a series of elongated, articulated segments or modules 20, 22, 24. Three such segments are shown in this embodiment, but one or more such segments could be used. As seen in FIG. 3, a first elongated heat transfer segment 20 is located at the proximal end of the heat transfer element 14. A mixing-inducing exterior surface of the segment 20 comprises four parallel helical ridges 28 with four parallel helical grooves 26 therebetween. One, two, three, or more parallel helical ridges 28 could also be used. In this embodiment, the helical ridges 28 and the helical grooves 26 of the heat transfer segment 20 have a left hand twist, referred to herein as a counter-clockwise spiral or helical rotation, as they proceed toward the distal end of the heat transfer segment 20.

The first heat transfer segment 20 is coupled to a second elongated heat transfer segment 22 by a first tube section 25, which provides flexibility. The second heat transfer segment 22 comprises one or more helical ridges 32 with one or more helical grooves 30 therebetween. The ridges 32 and grooves 30 have a right hand, or clockwise, twist as they proceed toward the distal end of the heat transfer segment 22. The second heat transfer segment 22 is coupled to a third elongated heat transfer segment 24 by a second tube section 27. The third heat transfer segment 24 comprises one or more helical ridges 36 with one or more helical grooves 34 therebetween. The helical ridge 36 and the helical groove 34 have a left hand, or counter-clockwise, twist as they proceed toward the distal end of the heat transfer segment 24. Thus, successive heat transfer segments 20, 22, 24 of the heat transfer element 14 alternate between having clockwise and counterclockwise helical twists. The actual left or right hand twist of any particular segment is immaterial, as long as adjacent segments have opposite helical twist.

In addition, the rounded contours of the ridges 28, 32, 36 also allow the heat transfer element 14 to maintain a relatively atraumatic profile, thereby minimizing the possibility of damage to the blood vessel wall. A heat transfer element may be comprised of one, two, three, or more heat transfer segments.

The tube sections 25, 27 are formed from seamless and nonporous materials, such as metal, and therefore are impermeable to gas, which can be particularly important, depending on the type of working fluid that is cycled through the heat transfer element 14. The structure of the tube sections 25, 27 allows them to bend, extend and compress, which increases the flexibility of the heat transfer element 14 so that it is more readily able to navigate through blood vessels. The tube sections 25, 27 are also able to tolerate cryogenic temperatures without a loss of performance. The tube sections 25, 27 may have a predetermined thickness of their walls, such as between about 0.5 and 0.8 mils. The predetermined thickness is to a certain extent dependent on the diameter of the overall tube. Thicknesses of 0.5 to 0.8 mils may be appropriate especially for a tubal diameter of about 4 mm. For smaller diameters, such as about 3.3 mm, larger thicknesses may be employed for higher strength. In another embodiment, tube sections 25, 27 may be formed from a polymer material such as rubber, e.g., latex rubber.

The exterior surfaces of the heat transfer element 14 can be made from metal except in flexible joint embodiments where the surface may be comprised of a polymer material. The metal may be a very high thermal conductivity material such as nickel, thereby facilitating efficient heat transfer. Alternatively, other metals such as stainless steel, titanium, aluminum, silver, copper and the like, can be used, with or without an appropriate coating or treatment to enhance biocompatibility or inhibit clot formation. Suitable biocompatible coatings include, e.g., gold, platinum or polymer paralyene. The heat transfer element 14 may be manufactured by plating a thin layer of metal on a mandrel that has the appropriate pattern. In this way, the heat transfer element 14 may be manufactured inexpensively in large quantities, which is an important feature in a disposable medical device.

Because the heat transfer element 14 may dwell within the blood vessel for extended periods of time, such as 24–48 hours or even longer, it may be desirable to treat the surfaces of the heat transfer element 14 to avoid clot formation. One means by which to prevent thrombus formation is to bind an antithrombogenic agent to the surface of the heat transfer element 14. For example, heparin is known to inhibit clot formation and is also known to be useful as a biocoating. Alternatively, the surfaces of the heat transfer element 14 may be bombarded with ions such as nitrogen. Bombardment with nitrogen can harden and smooth the surface and thus prevent adherence of clotting factors to the surface.

Figures 4, 5:
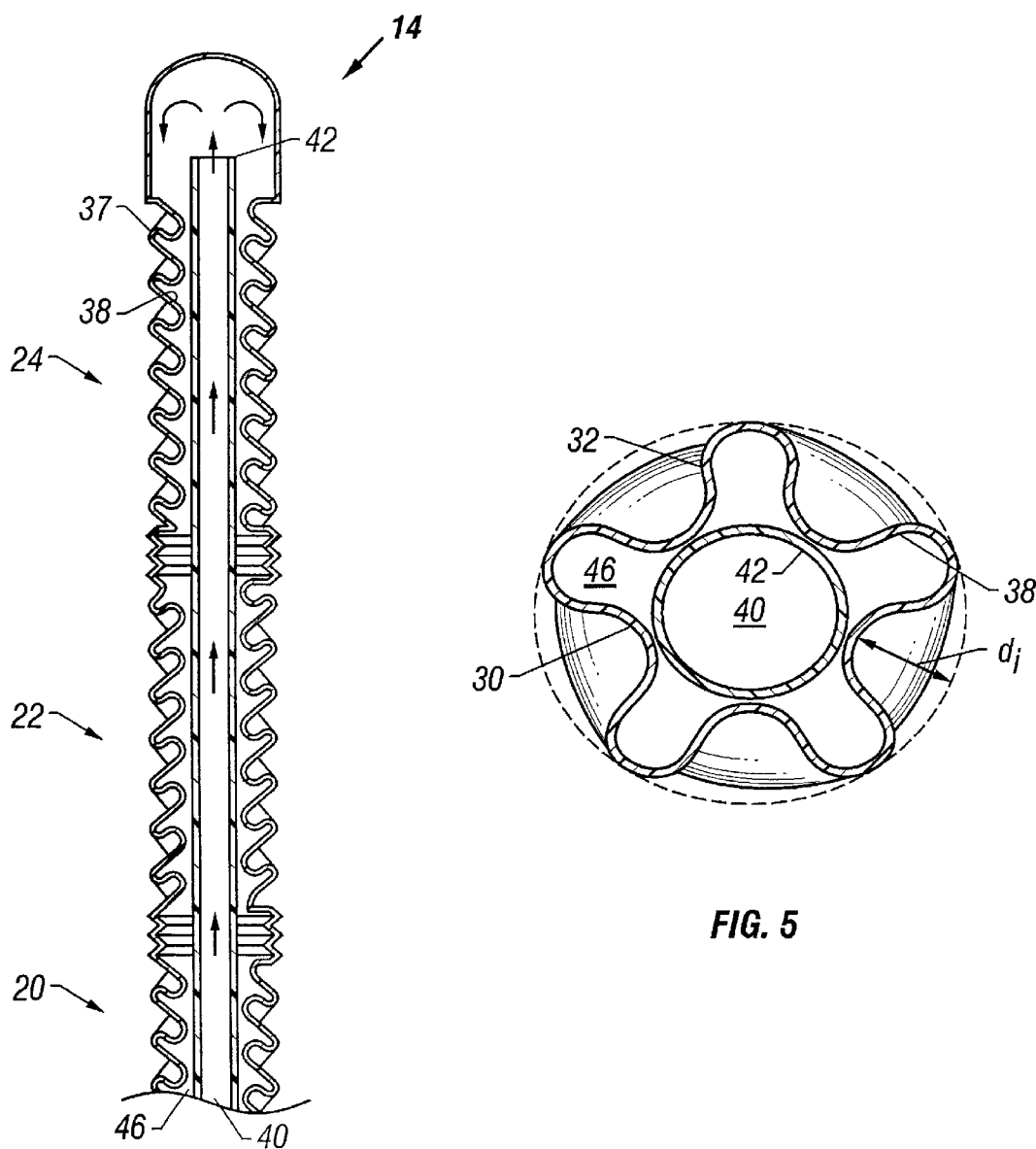
FIG. 4 is a front sectional view of the heat transfer element of FIG. 1.
FIG. 5 is a transverse sectional view of the heat transfer element of FIG. 1.

FIG. 4 is a longitudinal sectional view of the heat transfer element 14, taken along line 4—4 in FIG. 3. Some interior contours are omitted for purposes of clarity. An inner tube 42 creates an inner coaxial lumen 40 and an outer coaxial lumen 46 within the heat transfer element 14. Once the heat transfer element 14 is in place in the blood vessel, a working fluid such as saline or other aqueous solution may be circulated through the heat transfer element 14. Fluid flows up a supply catheter into the inner coaxial lumen 40. At the distal end of the heat transfer element 14, the working fluid exits the inner coaxial lumen 40 and enters the outer lumen 46. As the working fluid flows through the outer lumen 46, heat is transferred between the working fluid and the exterior surface 37 of the heat transfer element 14. Because the heat transfer element 14 is constructed from a high conductivity material, the temperature of its exterior surface may approach the temperature of the working fluid. The tube 42 may be formed as an insulating divider to thermally separate the inner lumen 40 from the outer lumen 46. For example, insulation may be achieved by creating longitudinal air channels in the wall of the insulating tube 42. Alternatively, the insulating tube 42 may be constructed of a non-thermally conductive material like polytetrafluoroethylene or some other polymer.

It is important to note that the same mechanisms that govern the heat transfer rate between the exterior surface 37 of the heat transfer element 14 and the blood also govern the heat transfer rate between the working fluid and the interior surface 38 of the heat transfer element 14. The heat transfer characteristics of the interior surface 38 are particularly important when using water, saline or other fluid which remains a liquid as the coolant. Other coolants such as freon undergo nucleate boiling and create turbulence through a different mechanism. Saline is a safe coolant because it is nontoxic, and leakage of saline does not result in a gas embolism, which could occur with the use of boiling refrigerants. Since turbulence or mixing in the coolant is enhanced by the shape of the interior surface 38 of the heat transfer element 14, the coolant can be delivered to the heat transfer element 14 at a warmer temperature and still achieve the necessary heat transfer rate.

This has a number of beneficial implications in the need for insulation along the catheter shaft length. Due to the decreased need for insulation, the catheter shaft diameter can be made smaller. The enhanced heat transfer characteristics of the interior surface of the heat transfer element 14 also allow the working fluid to be delivered to the heat transfer element 14 at lower flow rates and lower pressures. High pressures may make the heat transfer element stiff and cause it to push against the wall of the blood vessel, thereby shielding part of the exterior surface 37 of the heat transfer element 14 from the blood. Because of the increased heat transfer characteristics achieved by the alternating helical ridges 28, 32, 36, the pressure of the working fluid may be as low as 5 atmospheres, 3 atmospheres, 2 atmospheres or even less than 1 atmosphere.

FIG. 5 is a transverse sectional view of the heat transfer element 14, taken at a location denoted by the line 5—5 in FIG. 3. FIG. 5 illustrates a five-lobed embodiment, whereas FIG. 3 illustrates a four-lobed embodiment. As mentioned earlier, any number of lobes might be used. In FIG. 5, the coaxial construction of the heat transfer element 14 is clearly shown. The inner coaxial lumen 40 is defined by the insulating coaxial tube 42. The outer lumen 46 is defined by the exterior surface of the insulating coaxial tube 42 and the interior surface 38 of the heat transfer element 14. In addition, the helical ridges 32 and helical grooves 30 may be seen in FIG. 5. In the preferred embodiment, the depth of the grooves, $d_i$, may be greater than the boundary layer thickness which would have developed if a cylindrical heat transfer element were introduced, For example, in a heat transfer element 14 with a 4 mm outer diameter, the depth of the invaginations, $d_i$, may be approximately equal to 1 mm if designed for use in the carotid artery. Although FIG. 5 shows four ridges and four grooves, the number of ridges and grooves may vary. Thus, heat transfer elements with 1, 2, 3, 4, 5, 6, 7, 8 or more ridges are specifically contemplated.

Figure 6:
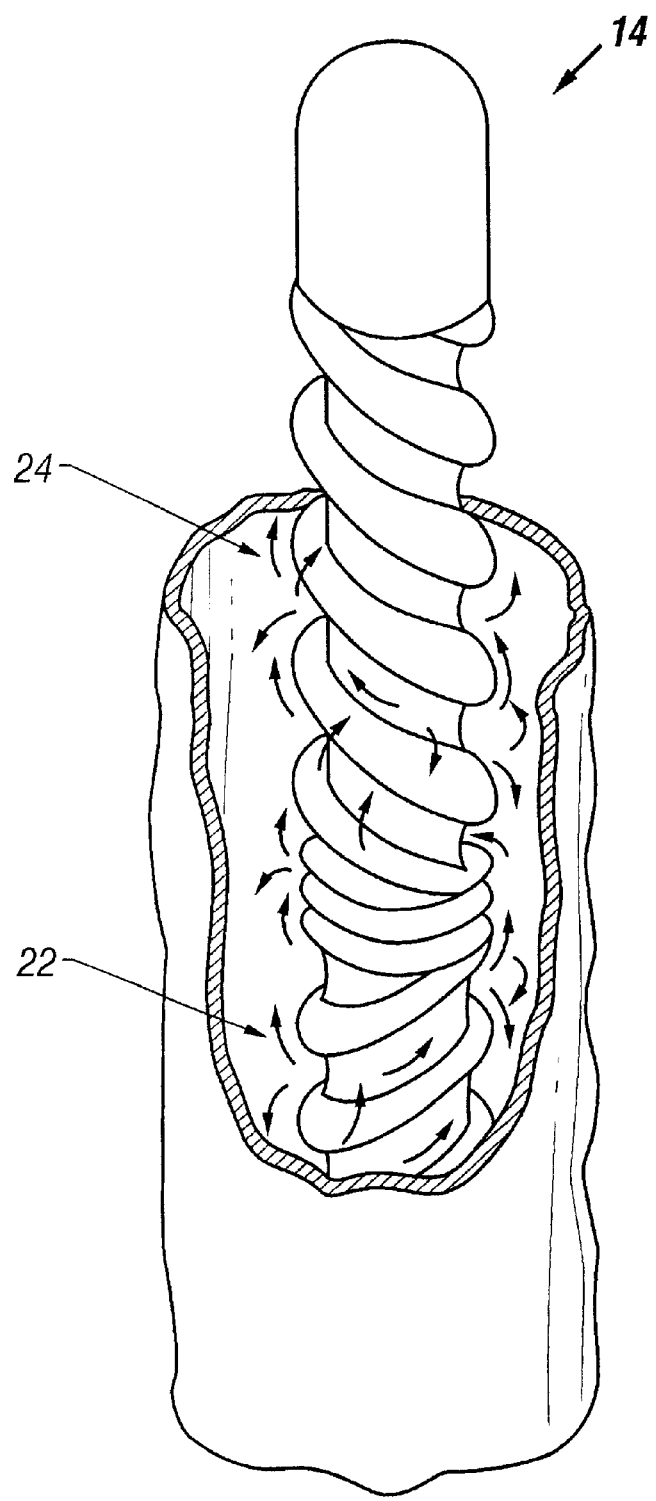
FIG. 6 is a front perspective view of the heat transfer element of FIG. 1 in use within a partially broken away blood vessel.

FIG. 6 is a perspective view of a heat transfer element 14 in use within a blood vessel, showing only one helical lobe per segment for purposes of clarity. Beginning from the proximal end of the heat transfer element (not shown in FIG. 6), as the blood moves forward during the systolic pulse, the first helical heat transfer segment 20 induces a counter-clockwise rotational inertia to the blood. As the blood reaches the second segment 22, an unstable shear layer is produced that causes mixing within the blood. Further, as the blood reaches the third segment 24, the rotational direction of the inertia is again reversed. The sudden changes in flow direction actively reorient and randomize the velocity vectors, thus ensuring mixing throughout the bloodstream. During transitional to turbulent flow, the velocity vectors of the blood become more random and, in some cases, become perpendicular to the axis of the artery. In addition, as the velocity of the blood within the artery decreases and reverses direction during the cardiac cycle, additional mixing is induced and sustained throughout the duration of each pulse through the same mechanisms described above.

Thus, a large portion of the volume of warm blood in the vessel is actively brought in contact with the heat transfer element 14, where it can be cooled by direct contact rather than being cooled largely by conduction through adjacent laminar layers of blood. As noted above, the depth of the grooves 26, 30, 34 (FIG. 3) is greater than the depth of the boundary layer that would develop if a straight-walled heat transfer element were introduced into the blood stream. In this way, mixing is induced. In the preferred embodiment, in order to create the desired level of mixing in the entire blood stream during the whole cardiac cycle, the heat transfer element 14 creates a turbulence intensity greater than about 0.05. The turbulence intensity may be greater than 0.05, 0.06, 0.07 or up to 0.10 or 0.20 or greater.

Referring back to FIG. 3, the heat transfer element 14 has been designed to address all of the design criteria discussed above. First, the heat transfer element 14 is flexible and is made of a highly conductive material. The flexibility is provided by a segmental distribution of tube sections 25, 27 which provide an articulating mechanism. The tube sections have a predetermined thickness which provides sufficient flexibility. Second, the exterior surface area 37 has been increased through the use of helical ridges 28, 32, 36 and helical grooves 26, 30, 34. The ridges also allow the heat transfer element 14 to maintain a relatively atraumatic profile, thereby minimizing the possibility of damage to the vessel wall. Third, the heat transfer element 14 has been designed to promote mixing both internally and externally. The modular or segmental design allows the direction of the invaginations to be reversed between segments. The alternating helical rotations create an alternating flow that results in a mixing of the blood in a manner analogous to the mixing action created by the rotor of a washing machine that switches directions back and forth. This mixing action is intended to promote a high level of mixing or turbulent kinetic energy to enhance the heat transfer rate. The alternating helical design also causes beneficial mixing, or turbulent kinetic energy, of the working fluid flowing internally.

Figure 7:
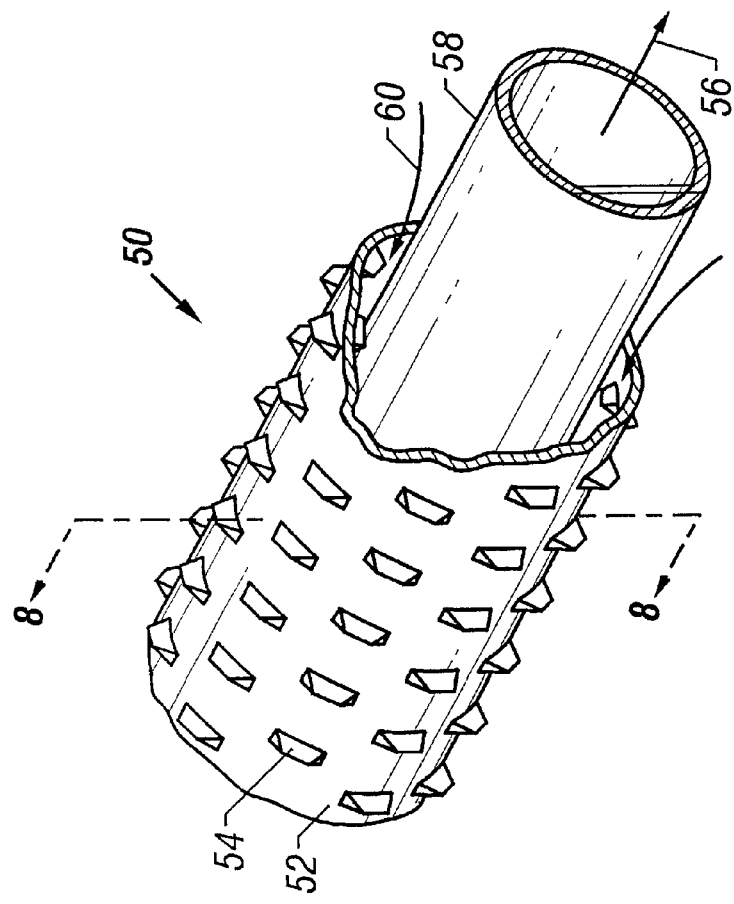
FIG. 7 is a partially broken away front perspective view of a second embodiment of a mixing-inducing heat transfer element according to the principles of the invention.

FIG. 7 is a cut-away perspective view of an alternative embodiment of a heat transfer element 50. An external surface 52 of the heat transfer element 50 is covered with a series of axially staggered protrusions 54. The staggered nature of the outer protrusions 54 is readily seen with reference to FIG. 8 which is a transverse cross-sectional view taken at a location denoted by the line 8—8 in FIG. 7. In order to induce free stream turbulence, the height, $d_p$, of the staggered outer protrusions 54 is greater than the thickness of the boundary layer which would develop if a smooth heat transfer element had been introduced into the blood stream. As the blood flows along the external surface 52, it collides with one of the staggered protrusions 54 and a turbulent wake flow is created behind the protrusion. As the blood divides and swirls along side of the first staggered protrusion 54, its turbulent wake encounters another staggered protrusion 54 within its path preventing the re-lamination of the flow and creating yet more mixing. In this way, the velocity vectors are randomized and mixing is created not only in the boundary layer but also throughout the free stream. As is the case with the preferred embodiment, this geometry also induces a mixing effect on the internal coolant flow.

Figure 8:
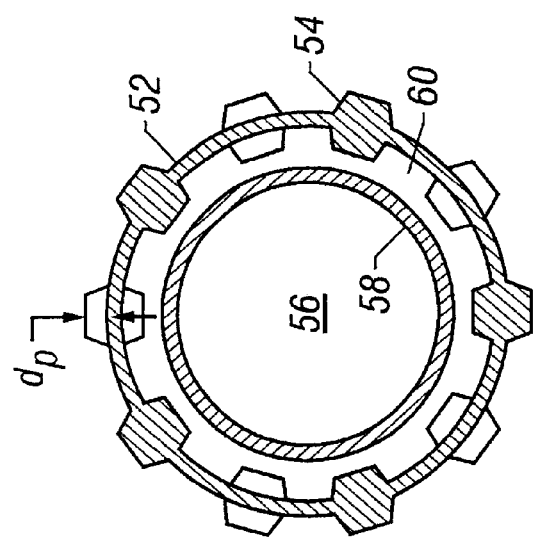
FIG. 8 is a transverse sectional view of the heat transfer element of FIG. 7.

A working fluid is circulated up through an inner coaxial lumen 56 defined by an insulating coaxial tube 58 to a distal tip of the heat transfer element 50. The working fluid then traverses an outer coaxial lumen 60 in order to transfer heat to the exterior surface 52 of the heat transfer element 50. The inside surface of the heat transfer element 50 is similar to the exterior surface 52, in order to induce mixing flow of the working fluid. The inner protrusions can be aligned with the outer protrusions 54, as shown in FIG. 8, or they can be offset from the outer protrusions 54, as shown in FIG. 7.

Figure 9:
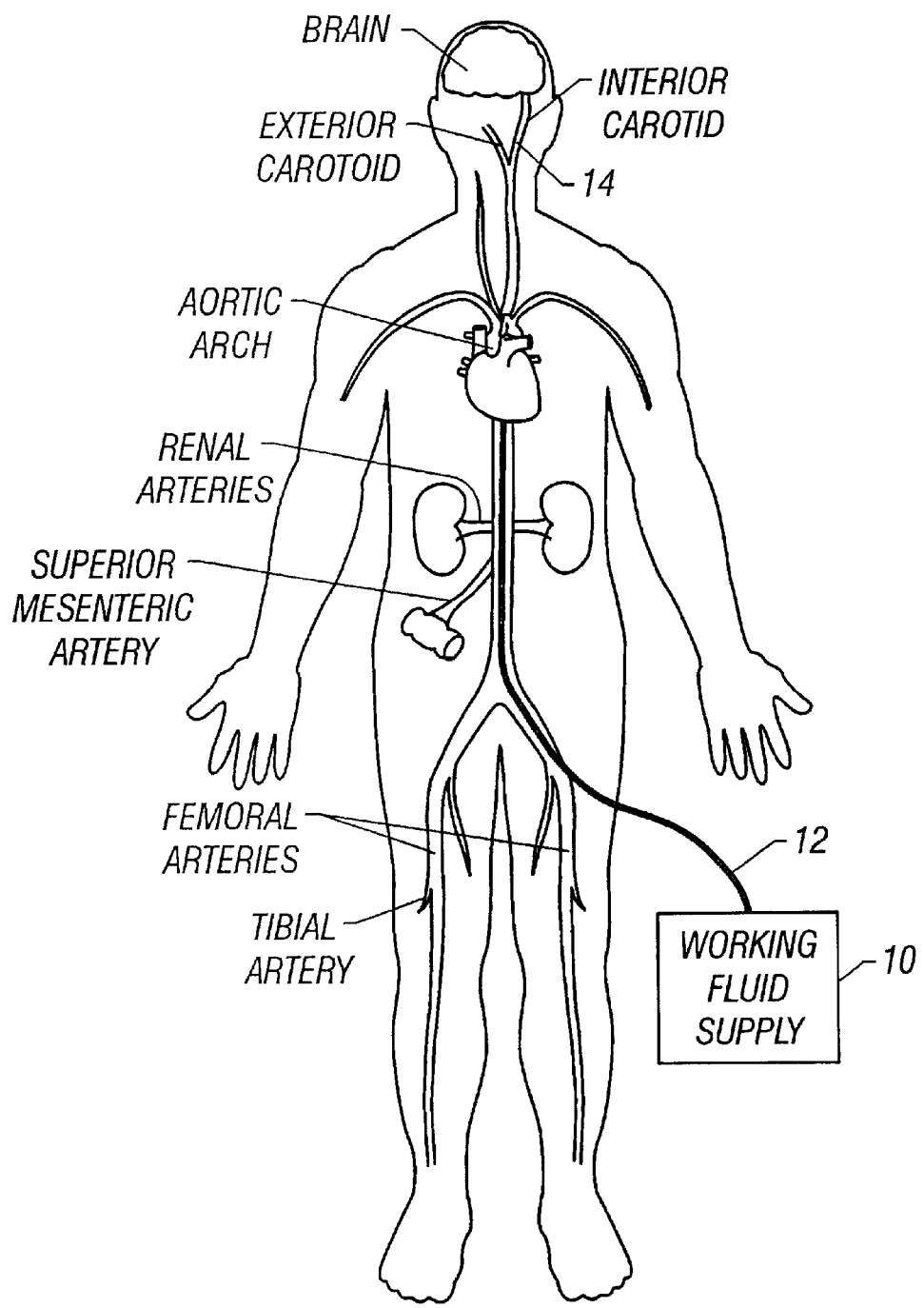
FIG. 9 is a schematic representation of the invention being used to cool the brain of a patient.

FIG. 9 is a schematic representation of an embodiment of the invention being used to cool the brain of a patient. A selective organ hypothermia apparatus shown in FIG. 9 includes a working fluid supply 10, preferably supplying a chilled liquid such as water, alcohol or a halogenated hydrocarbon, a supply catheter 12 and the heat transfer element 14. The supply catheter 12 has a coaxial construction. An inner coaxial lumen within the supply catheter 12 receives coolant from the working fluid supply 10. The coolant travels the length of the supply catheter 12 to the heat transfer element 14 which serves as the cooling tip of the catheter. At the distal end of the heat transfer element 14, the coolant exits the insulated interior lumen and traverses the length of the heat transfer element 14 in order to decrease the temperature of the heat transfer element 14. The coolant then traverses an outer lumen of the supply catheter 12 so that it may be disposed of or recirculated. The supply catheter 12 is a flexible catheter having a diameter sufficiently small to allow its distal end to be inserted percutaneously into an accessible artery such as the femoral artery of a patient as shown in FIG. 9. The supply catheter 12 is sufficiently long to allow the heat transfer element 14 at the distal end of the supply catheter 12 to be passed through the vascular system of the patient and placed in the internal carotid artery or other small artery. The method of inserting the catheter into the patient and routing the heat transfer element 14 into a selected artery is well known in the art. A mentioned above, the device may also be placed in the venous system to cause total body cooling. The device's helices, which are one way of increasing the surface area as well as to induce mixing or turbulence, enhance heat transfer.

Although the working fluid supply 10 is shown as an exemplary cooling device, other devices and working fluids may be used. For example, in order to provide cooling, freon, perflourocarbon, water, or saline may be used, as well as other such coolants.

The heat transfer element can absorb or provide over 75 Watts of heat to the blood stream and may absorb or provide as much as 100 Watts, 150 Watts, 170 Watts or more. For example, a heat transfer element with a diameter of 4 mm and a length of approximately 10 cm using ordinary saline solution chilled so that the surface temperature of the heat transfer element is approximately 5° C. and pressurized at 2 atmospheres can absorb about 100 Watts of energy from the bloodstream. Smaller geometry heat transfer elements may be developed for use with smaller organs which provide 60 Watts, 50 Watts, 25 Watts or less of heat transfer. For venous cooling, as much as or more than 250 Watts may be extracted.

An exemplary practice of the present invention, for arterial applications, is illustrated in the following non-limiting example.

Exemplary Procedure

1. The patient is initially assessed, resuscitated, and stabilized.

2. The procedure is carried out in an angiography suite or surgical suite equipped with fluoroscopy.

3. Because the catheter is placed into the common carotid artery, it is important to determine the presence of stenotic atheromatous lesions. A carotid duplex (Doppler/ultrasound) scan can quickly and non-invasively make this determination. The ideal location for placement of the catheter is in the left carotid so this may be scanned first. If disease is present, then the right carotid artery can be assessed. This test can be used to detect the presence of proximal common carotid lesions by observing the slope of the systolic upstroke and the shape of the pulsation. Although these lesions are rare, they could inhibit the placement of the catheter. Examination of the peak blood flow velocities in the internal carotid can determine the presence of internal carotid artery lesions. Although the catheter is placed proximally to such lesions, the catheter may exacerbate the compromised blood flow created by these lesions. Peak systolic velocities greater that 130 cm/sec and peak diastolic velocities>100 cm/sec in the internal indicate the presence of at least 70% stenosis. Stenosis of 70% or more may warrant the placement of a stent to open up the internal artery diameter.

4. The ultrasound can also be used to determine the vessel diameter and the blood flow and the catheter with the appropriately sized heat transfer element are selected.

5. After assessment of the arteries, the patient's inguinal region is sterilely prepped and infiltrated with lidocaine.

6. The femoral artery is cannulated and a guide wire may be inserted to the desired carotid artery. Placement of the guide wire is confirmed with fluoroscopy.

7. An angiographic catheter can be fed over the wire and contrast media injected into the artery to further to assess the anatomy of the carotid.

8. Alternatively, the femoral artery is cannulated and a 10–12.5 french (f) introducer sheath is placed.

9. A guide catheter is placed into the desired common carotid artery. If a guiding catheter is placed, it can be used to deliver contrast media directly to further assess carotid anatomy.

10. A 10 f–12 f (3.3–4.0 mm) (approximate) cooling catheter is subsequently filled with saline and all air bubbles are removed.

11. The cooling catheter is placed into the carotid artery via the guiding catheter or over the guidewire. Placement is confirmed with fluoroscopy.

12. The cooling catheter is connected to a refrigerated pump circuit also filled with saline and free from air bubbles.

13. Cooling is initiated by starting the refrigerated pump circuit. The saline within the cooling catheter is circulated at 3–8 cc/sec. The saline travels through the refrigerated pump circuit and is cooled to approximately 1° C.

14. The saline subsequently enters the cooling catheter where it is delivered to the heat transfer element. The saline is warmed to approximately 5–7° C. as it travels along the inner lumen of the catheter shaft to the end of the heat transfer element.

15. The saline then flows back through the heat transfer element in contact with the inner metallic surface. The saline is further warmed in the heat transfer element to 12–15° C., and in the process, heat is absorbed from the blood, cooling the blood to 30° C. to 32° C.

16. The chilled blood then goes on to chill the brain. It is estimated that 15–30 minutes will be required to cool the brain to 30 to 32° C.

17. The warmed saline travels back down the outer lumen of the catheter shaft and back to the chilled water bath where it is cooled to 1° C.

18. The pressure drops along the length of the circuit are estimated to be, e.g., 6 atmospheres.

19. The cooling can be adjusted by increasing or decreasing the flow rate of the saline, or by changing the temperature of the saline. Monitoring of the temperature drop of the saline along the heat transfer element will allow the flow to be adjusted to maintain the desired cooling effect.

20. The catheter is left in place to provide cooling for up to or more than 12 to 24 hours.

21. If desired, warm saline can be circulated to promote warming of the brain at the end of the procedure.

Figure 10:
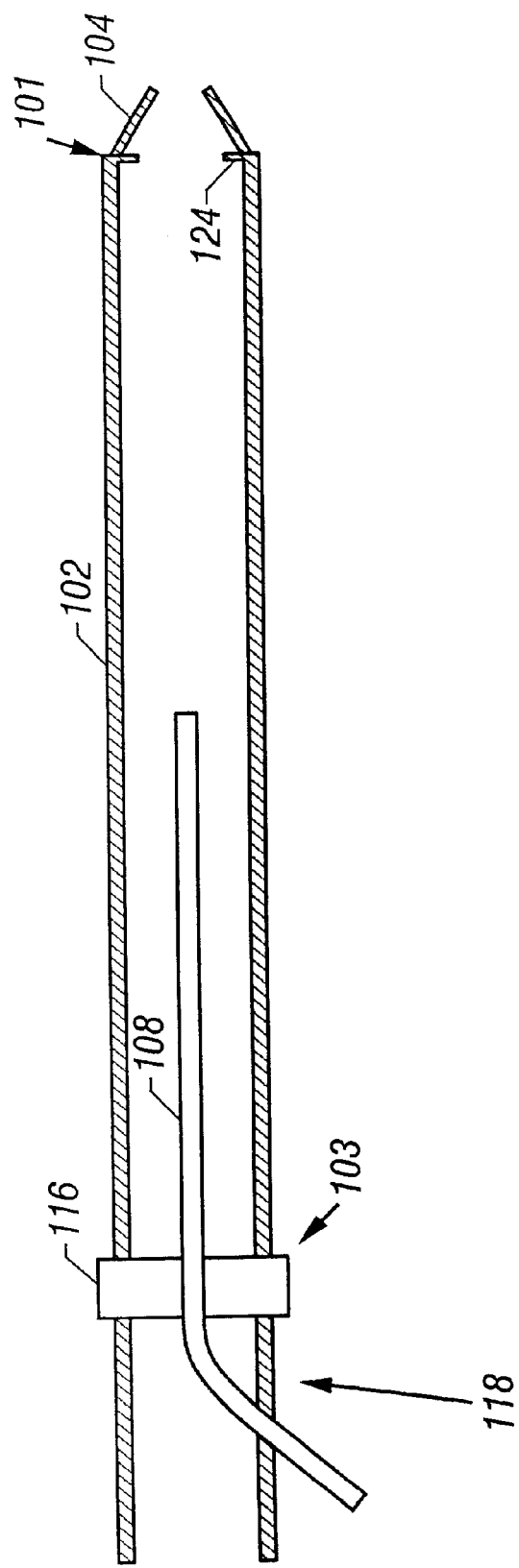
FIG. 10 is a front sectional view of a guide catheter according to an embodiment of the invention which may be employed for applications of the heat transfer element according to the principles of the invention.

The invention may also be used in combination with other techniques. For example, one technique employed to place working lumens or catheters in desired locations employs guide catheters, as mentioned above. Referring to FIG. 10, a guide catheter 102 is shown which may be advantageously employed in the invention. The guide catheter 102 has a soft tapered tip 104 and a retaining flange 124 at a distal end 101. The soft tapered tip 104 allows an atraumatic entrance of the guide catheter 102 into an artery as well as a sealing function as is described in more detail below. The retaining flange 124 may be a metallic member adhered to the guide catheter interior wall or may be integral with the material of the tube. The retaining flange 124 further has a sealing function described in more detail below.

The guide catheter 102 may have various shapes to facilitate placement into particular arteries. In the case of the carotid artery, the guide catheter 102 may have the shape of a hockey stick. The guide catheter 102 may include a Pebax® tube with a Teflon® liner. The Teflon® liner provides sufficient lubricity to allow minimum friction when components are pushed through the tube. A metal wire braid may also be employed between the Pebax® tube and the Teflon® liner to provide torqueability of the guide catheter 102.

A number of procedures may be performed with the guide catheter 102 in place within an artery or vein. For example, a stent may be disposed across a stenotic lesion in the internal carotid artery. This procedure involves placing a guide wire through the guide catheter 102 and across the lesion. A balloon catheter loaded with a stent is then advanced along the guide wire. The stent is positioned across the lesion. The balloon is expanded with contrast, and the stent is deployed intravascularly to open up the stenotic lesion. The balloon catheter and the guide wire may then be removed from the guide catheter.

A variety of treatments may pass through the guide catheter. For example, the guide catheter, or an appropriate lumen disposed within, may be employed to transfer contrast for diagnosis of bleeding or arterial blockage, such as for angiography. The same may further be employed to deliver various drug therapies, e.g., to the brain. Such therapies may include delivery of thrombolytic drugs that lyse clots lodged in the arteries of the brain.

A proximal end 103 of the guide catheter 102 has a male luer connector for mating with a y-connector 118 attached to a supply tube 108. The supply tube 108 may include a braided Pebax® tube or a polyimide tube. The y-connector 118 connects to the guide catheter 102 via a male/female luer connector assembly 116. The y-connector 118 allows the supply tube 108 to enter the assembly and to pass through the male/female luer connector assembly 116 into the interior of the guide catheter 102. The supply tube 108 may be disposed with an outlet at its distal end. The outlet of the supply tube 108 may also be used to provide a working fluid to the interior of a heat transfer element 110. The guide catheter 102 may be employed as the return tube for the working fluid supply in this aspect of the invention. In this embodiment, a heat transfer element 110 is delivered to the distal end 101 of the guide catheter 102 as is shown in FIG. 11.

Figure 11:
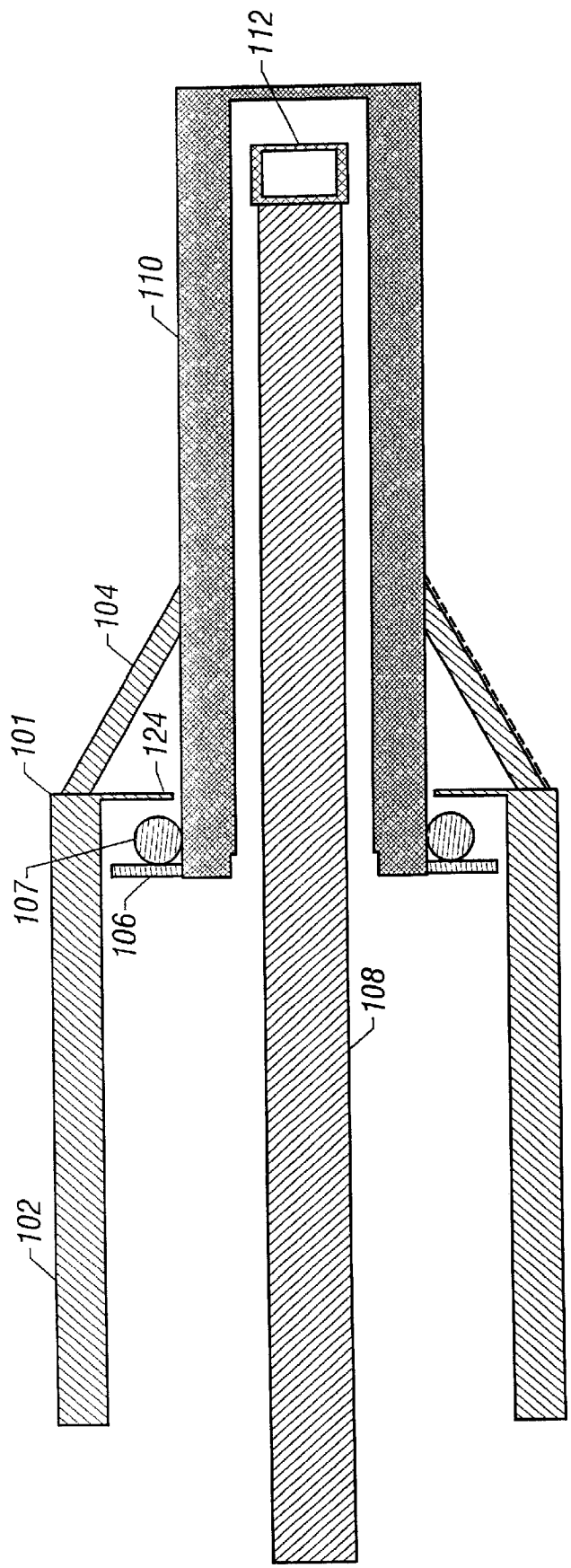
FIG. 11 is a front sectional view of a third embodiment of a catheter employing a heat transfer element according to the principles of the invention further employing a return tube/guide catheter.

In FIG. 11, the heat transfer element 110 is shown, nearly in a working location, in combination with the return tube/guide catheter 102. In particular, the heat transfer element 110 is shown near the distal end 101 of the return tube/guide catheter ("RTGC") 102. The heat transfer element 110 may be kept in place by a flange 106 on the heat transfer element 110 that abuts the retaining flange 124 on the RTGC 102. Flanges 124 and 106 may also employ o-rings such as an o-ring 107 shown adjacent to the flange 106. Other such sealing mechanisms or designs may also be used. In this way, the working fluid is prevented from leaking into the blood.

The supply tube 108 may connect to the heat transfer element 110 (the connection is not shown) and may be employed to push the heat transfer element 110 through the guide catheter 102. The supply tube should have sufficient rigidity to accomplish this function. In an alternative embodiment, a guide wire may be employed having sufficient rigidity to push both the supply tube 108 and the heat transfer element 110 through the guide catheter 102. So that the supply tube 108 is preventing from abutting its outlet against the interior of the heat transfer element 110 and thereby stopping the flow of working fluid, a strut 112 may be employed on a distal end of the supply tube 108. The strut 112 may have a window providing an alternative path for the flowing working fluid.

The heat transfer element 110 may employ any of the forms disclosed above, as well as variations of those forms. For example, the heat transfer element 110 may employ alternating helical ridges separated by flexible joints, the ridges creating sufficient mixing to enhance heat transfer between a working fluid and blood in the artery. Alternatively, the heat transfer element 110 may be inflatable and may have sufficient surface area such that the heat transfer due to conduction alone is sufficient to provide the requisite heat transfer. Details of the heat transfer element 110 are omitted in FIG. 11 for clarity.

Figure 12:
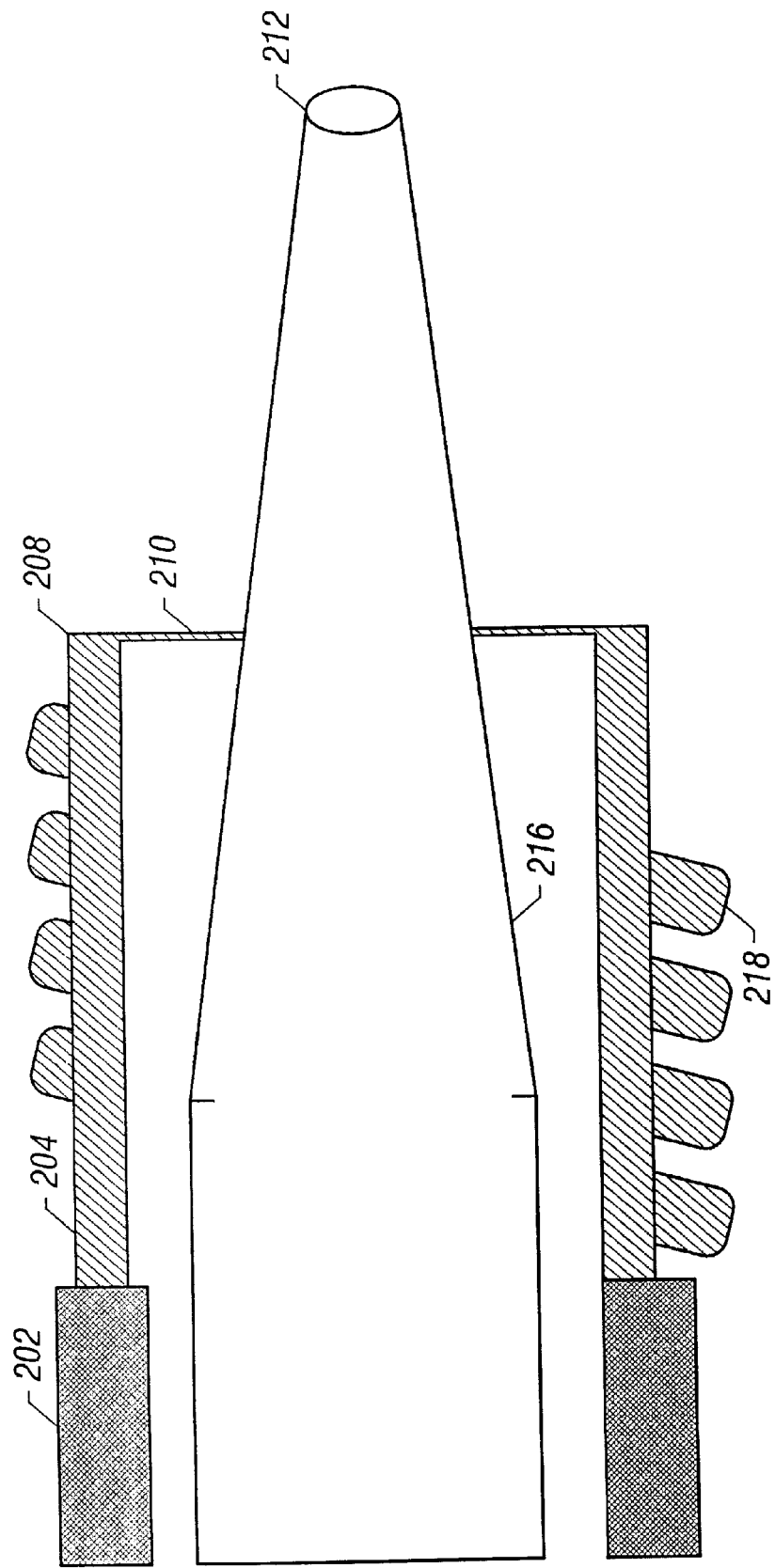
FIG. 12 is a front sectional view of a fourth embodiment of a catheter employing a heat transfer element according to the principles of the invention further employing a delivery catheter.

FIG. 12 shows an alternate embodiment of the invention in which a heat transfer element 204 employs an internal supply catheter 216. The heat transfer element 204 is shown with mixing-inducing invaginations 218 located thereon. Similar invaginations may be located in the interior of the heat transfer element 204 but are not shown for clarity.

Further, it should be noted that the heat transfer element 204 is shown with merely four invaginations. Other embodiments may employ multiple elements connected by flexible joints as is disclosed above. A single heat transfer element is shown in FIG. 12 merely for clarity.

A return supply catheter 202 is shown coupled to the heat transfer element 204. The return supply catheter may be coupled to the heat transfer element 204 in known fashion, and may provide a convenient return path for working fluid as may be provided to the heat transfer element 204 to provide temperature control of a flow or volume of blood.

A delivery catheter 216 is also shown in FIG. 12. The delivery catheter 216 may be coupled to a y-connector at its proximal end in the manner disclosed above. The delivery catheter 216 may be freely disposed within the interior of the return supply catheter 202 except where it is restrained from further longitudinal movement (in one direction) by a retaining flange 210 disposed at the distal end 208 of the heat transfer element 204. The delivery catheter 216 may be made sufficiently flexible to secure itself within retaining flange 210, at least for a short duration. The delivery catheter 216 may have a delivery outlet 212 at a distal end to allow delivery of a drug or other such material for therapeutic purposes. For example, a radioopaque fluid may be dispensed for angiography or a thrombolytic drug for thrombolytic applications.

For applications in which it is desired to provide drainage of the artery, e.g., laser ablation, the delivery catheter may be pulled upstream of the retaining flange 210, exposing an annular hole in fluid communication with the return supply catheter 202. The return supply catheter 202 may then be used to drain the volume adjacent the retaining flange 210.

Figure 13:
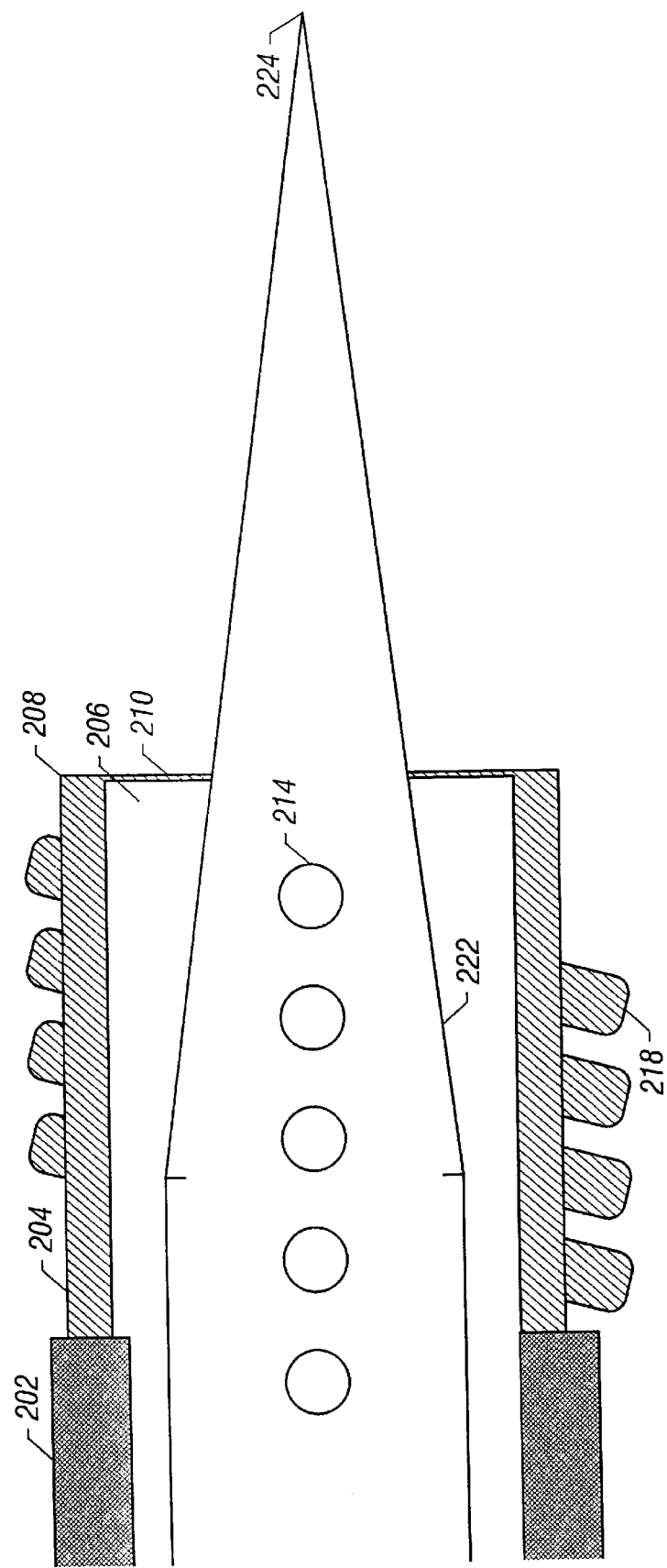
FIG. 13 is a front sectional view of the fourth embodiment of FIG. 12 further employing a working fluid catheter.

The assembly may also perform temperature control of blood in the artery where the same is located. Such temperature control procedures may be performed, e.g., before or after procedures involving the delivery catheter 216. Such a device for temperature control is shown in FIG. 13. In this figure, a working fluid catheter 222 is disposed within the return supply catheter 202 and the heat transfer element 204. In a manner similar to the delivery catheter 216, the working fluid catheter may be freely disposed within the interior of the return supply catheter 202 and may further be coupled to a y-connector at its proximal end in the manner disclosed above. The working fluid catheter 222 may further be made sufficiently flexible to secure itself within retaining flange 210, at least for a short duration. The working fluid catheter 222 may have a plurality of outlets 214 to allow delivery of a working fluid. The outlets 214 are located near the distal end 224 of the working fluid catheter 222 but somewhat upstream. In this way, the outlets 214 allow dispensation of a working fluid into the interior of the heat transfer element 204 rather than into the blood stream. The working fluid catheter 222 may also be insulated to allow the working fluid to maintain a desired temperature without undue heat losses to the walls of the working fluid catheter 222.

Figure 14:
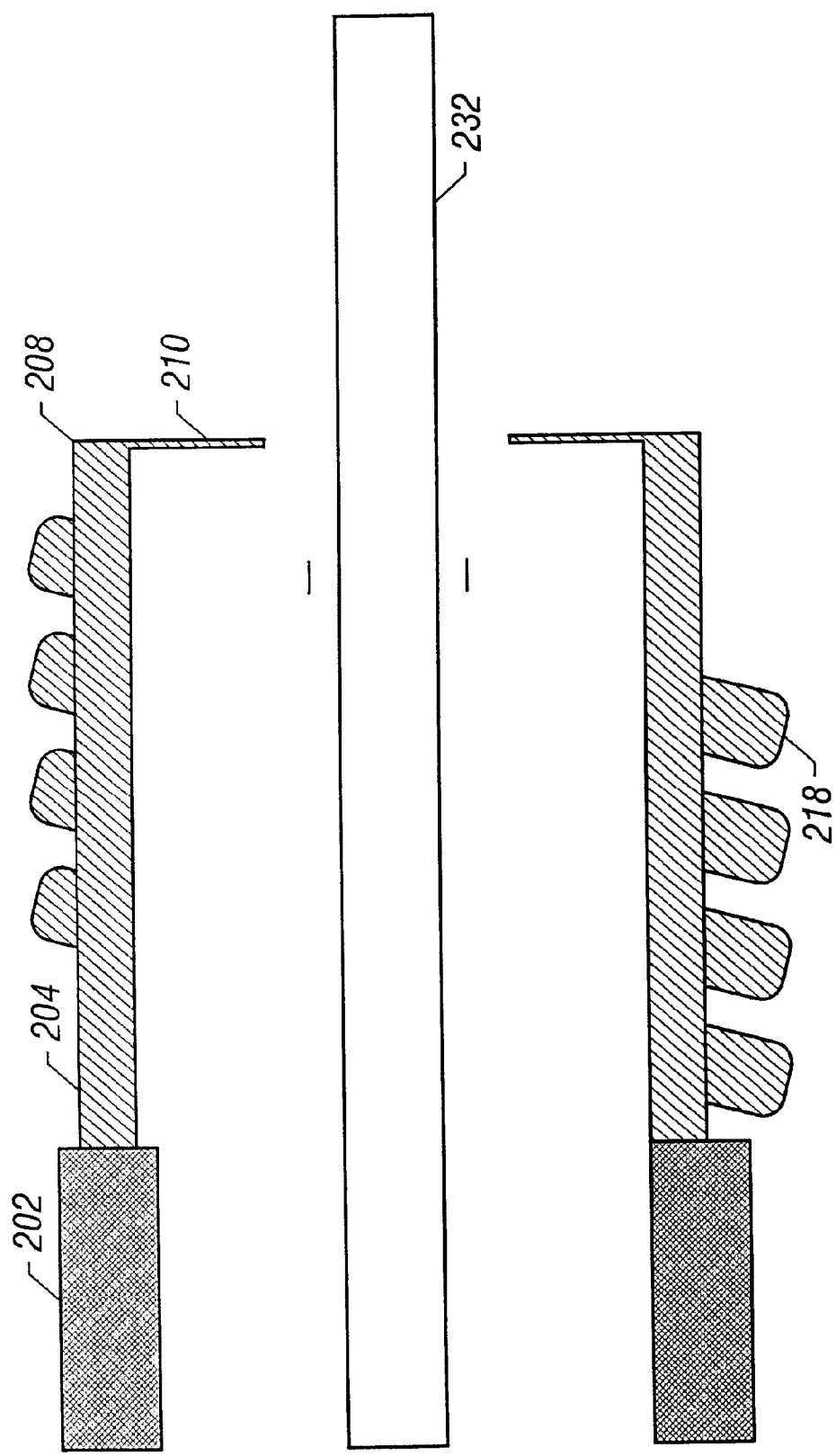
FIG. 14 is a front sectional view of a fifth embodiment of a catheter employing a heat transfer element according to the principles of the invention further employing a guide wire.

One method of disposing a heat transfer device within a desired artery, such as the carotid artery, involves use of a guide wire. Referring to FIG. 14, a guide wire 232 is shown disposed within the interior of the heat transfer element 204. The heat transfer element 204 may conveniently use the hole defined by retaining flange 210 to be threaded onto the guide wire 232.

Numerous other therapies may then employ the return supply catheter and heat transfer element as a "guide catheter". For example, various laser and ultrasound ablation catheters may be disposed within, as well as microcatheters. In this way, these therapeutic techniques may be employed at nearly the same time as therapeutic temperature control, including, e.g., neuroprotective cooling.

The use of an additional lumen was disclosed above in connection with passing a variety of treatments through the guide catheter. For example, an additional lumen may be employed to transfer contrast for diagnosis of bleeding or arterial blockage, such as for angiography. Such an additional lumen may be defined by a drug delivery catheter which forms a part of the overall catheter assembly. The same may be employed to deliver various drug therapies, e.g., to the brain. The use of an additional lumen was further mentioned in connection with expansion of a balloon that may be used to occlude a drug delivery lumen outlet.

Figure 15:
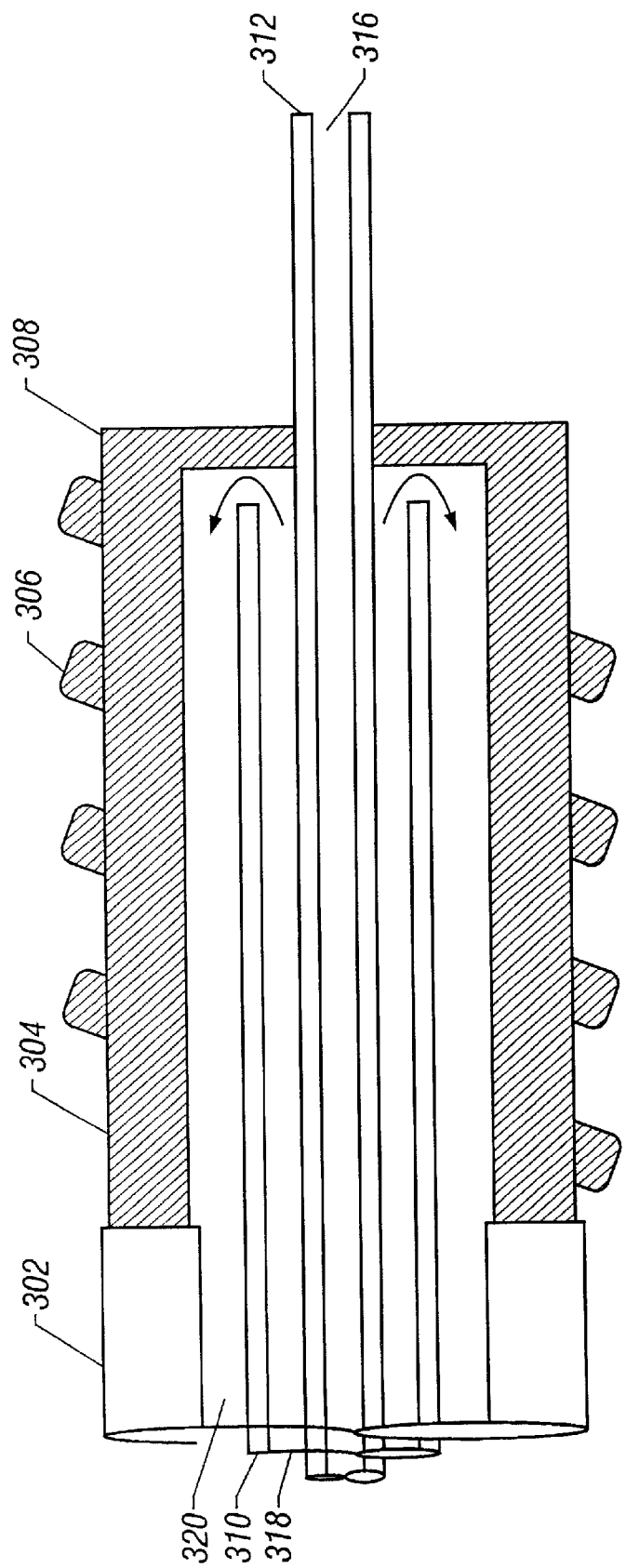
FIG. 15 is a front sectional view of a sixth embodiment of a catheter employing a heat transfer element according to the principles of the invention further employing a delivery lumen.

FIG. 15 depicts an implementation of an embodiment of the invention employing just such a third lumen. In FIG. 15, a third lumen 316 is a small central lumen defined by a drug delivery catheter substantially parallel to the supply and return catheters. A return catheter 302 defining an outlet lumen 320 is coupled to a heat transfer element 304 as before. The heat transfer element 304 may have mixing or turbulence-inducing invaginations 306 thereon. Within the heat transfer element 304 and the return catheter 302 is an inlet lumen 318 defined by a supply catheter 310. The inlet lumen 318 may be used to deliver a working fluid to the interior of the heat transfer element 304. The outlet lumen 320 may be used to return or exhaust the working fluid from the heat transfer element 304. As above, their respective functions may also be reversed. The radius of the return catheter may be greater or less (in the case where their roles are reversed) than the radius of the supply catheter. The working fluid may be used to heat or cool the heat transfer element which in turn heats or cools the fluid surrounding the heat transfer element.

A drug delivery catheter 312 defines the third lumen 316 and as shown may be coaxial with the inlet lumen 318 and the outlet lumen 320. Of course, the delivery catheter 312 may be also be off-axis or non-coaxial with respect to the inlet lumen 318 and the outlet lumen 320.

Figure 16:
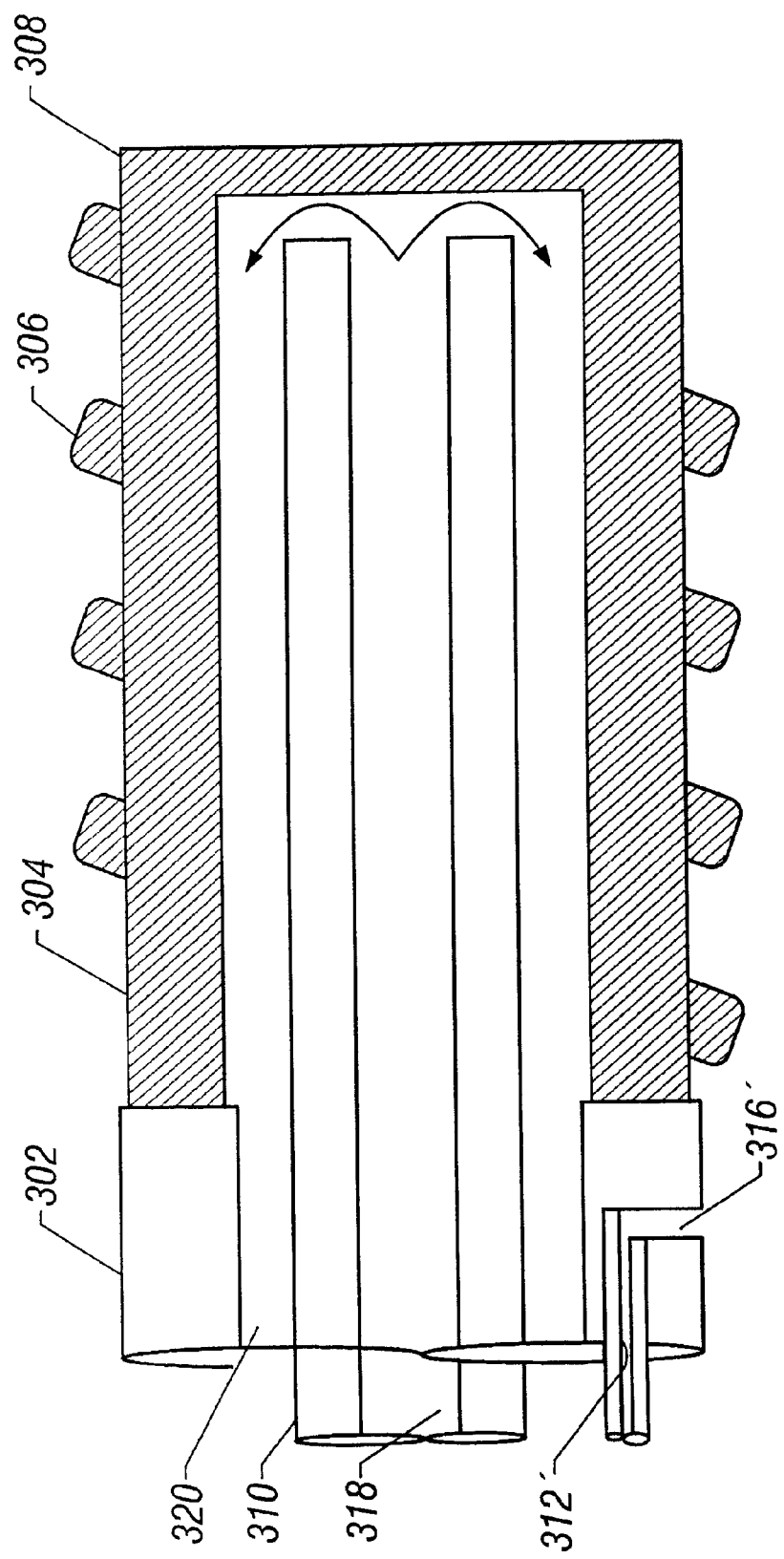
FIG. 16 is a front sectional view of an seventh embodiment of a catheter employing a heat transfer element according to the principles of the invention further employing a delivery lumen.
Figure 17:
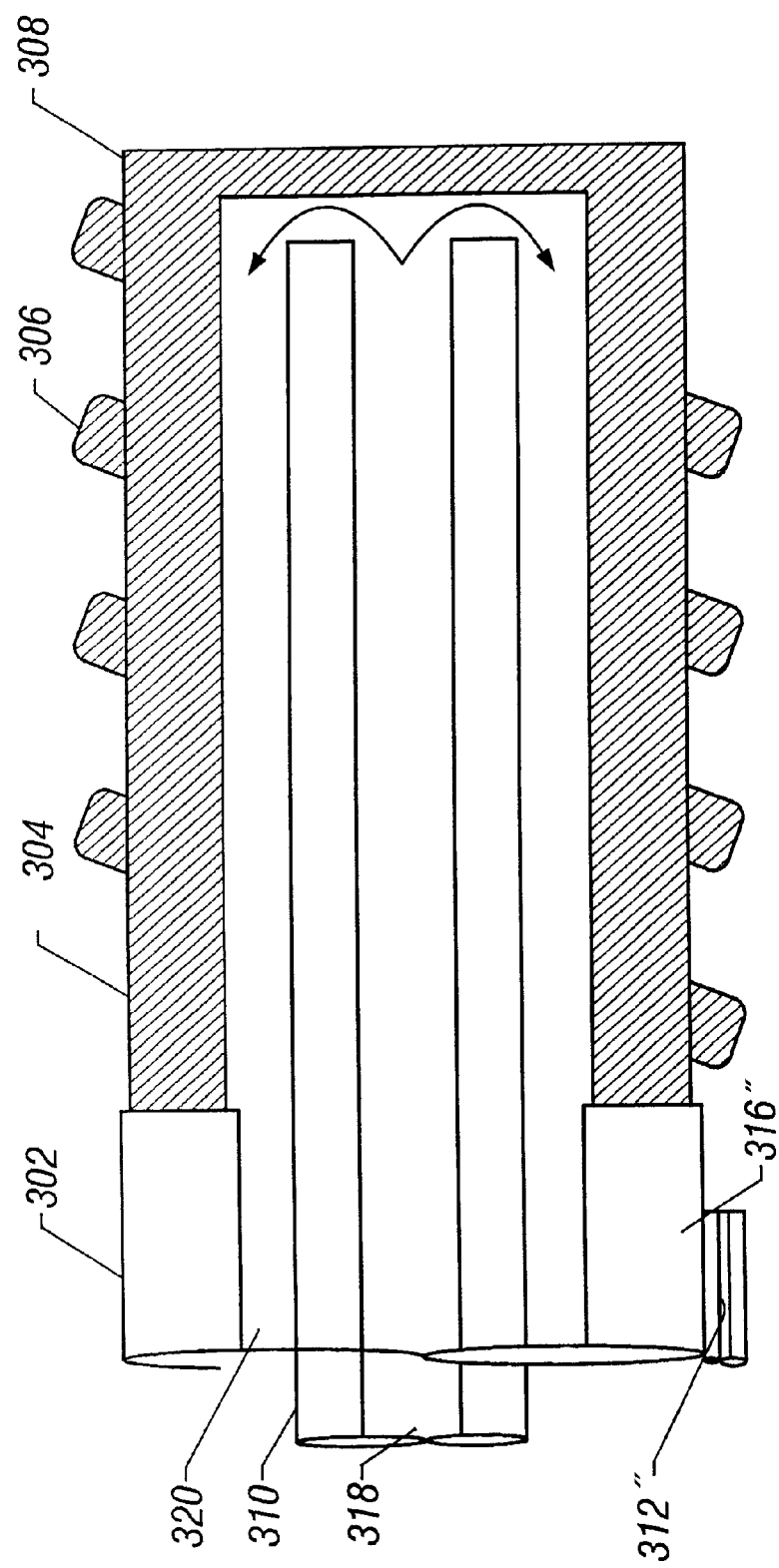
FIG. 17 is a front sectional view of an eighth embodiment of a catheter employing a heat transfer element according to the principles of the invention further employing a delivery lumen, this delivery lumen non-coaxial with the central body of the catheter.

For example, as shown in FIG. 16, the drug delivery catheter may be a lumen 316' within the return catheter and may be further defined by a catheter wall 312'. As another example, as shown in FIG. 17, the drug delivery catheter may be a lumen 316" adjacent to and parallel to the return catheter and may be further defined by a catheter wall 312". In an alternative embodiment, more than one lumen may be provided within the return catheter to allow delivery of several types of products, e.g., thrombolytics, saline solutions, etc. Of course, the supply catheter may also be used to define the drug delivery catheter. The drug delivery catheter may be substantially parallel to the return catheter or supply catheter or both, or may alternatively be at an oblique angle. The drug delivery catheter includes an outlet at a distal end thereof. The outlet may be distal or proximal of the distal end of the return or supply catheters. The outlet may be directed parallel to the return and supply catheters or may alternatively be directed transverse of the return and supply catheters.

The device may be inserted in a selected feeding vessel in the vascular system of a patient. For example, the device may be inserted in an artery which feeds a downstream organ or which feeds an artery which, in turn, feeds a downstream organ. In any of the embodiments of FIGS. 15–17, the drug delivery catheter lumen may be used to deliver a drug, liquid, enzyme or other material to the approximate location of the heat transfer element. Such delivery may occur before, after, or contemporaneous with heat transfer to or from the blood. For example, materials, e.g., drugs, liquids, enzymes, which operate at temperatures other than normal body temperature may be used by first altering the local blood temperature with the heat transfer element and then delivering the temperature specific material, e.g., a temperature-specific thrombolytic, which then operates at the altered temperature. Alternatively, such "third" lumens (with the supply and return catheters for the working fluid defining "first" and "second" lumens) may be used to remove particles, debris, or other desired products from the blood stream.

Figure 18:
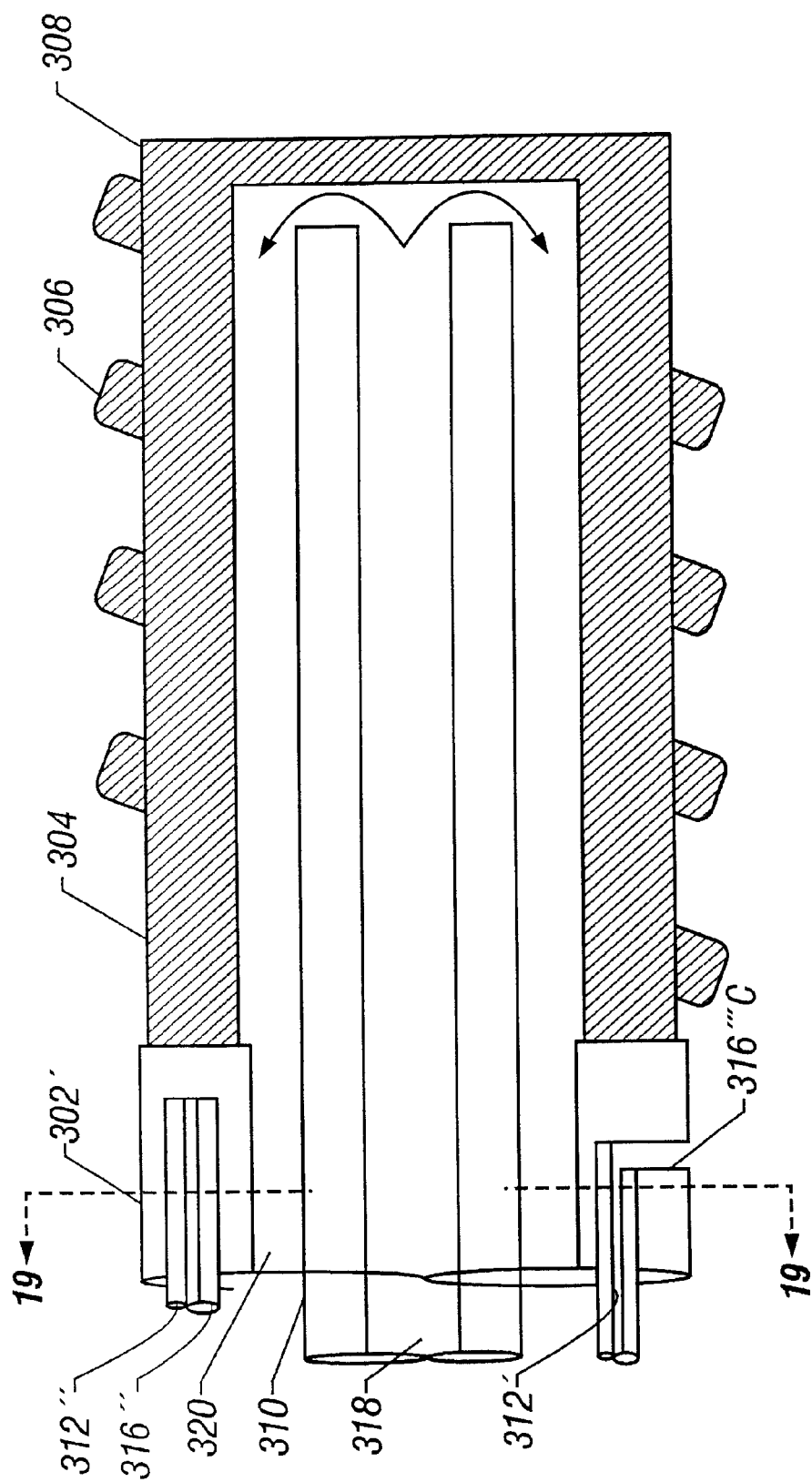
FIG. 18 is a front sectional view of a ninth embodiment of a catheter employing a heat transfer element according to the principles of the invention further employing multiple lumens.
Figure 19:
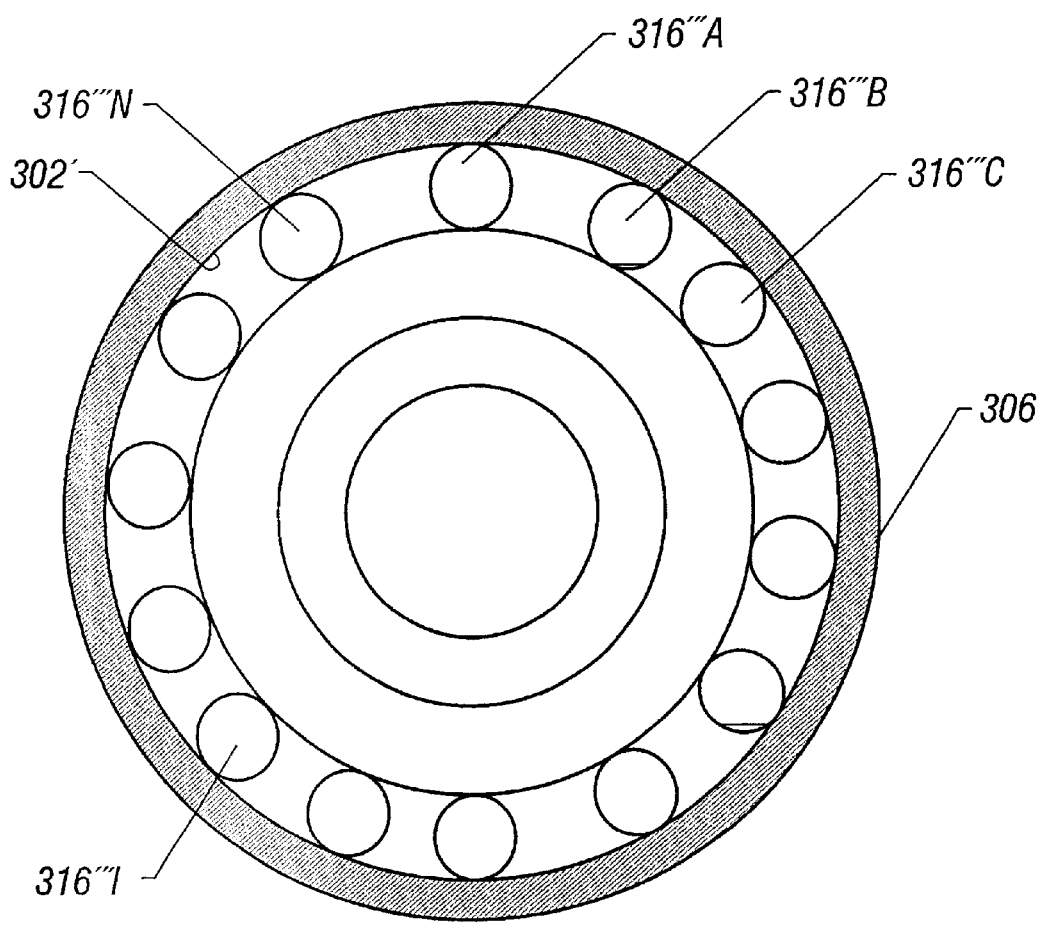
FIG. 19 is a cross-sectional view of the ninth embodiment of FIG. 18, taken along lines 19—19 of FIG. 18.

FIGS. 18 and 19 show another embodiment of the invention that is related to the embodiment of FIG. 16. In this embodiment, several additional sealed lumens are disposed in the return catheter. Some of the lumens may be for drug delivery and others may be used to enhance mixing in a manner described below. The sealed lumens are in pressure communication with a supply of air to inflate the same. In FIG. 18, a return catheter 302' has one lumen 316'''C as shown for drug delivery. Another, lumen 316'''I, is shown which may be employed to alter the geometry and shape of the overall catheter. That is, inflating lumen 316'''I causes the lumen to expand in the same way that inflating a balloon causes it to expand. In order to allow for the expansion, appropriately reduced return catheter wall thicknesses may be employed. Also, inflatable lumens 316'''A–B and 316'''D–N may be distributed in a substantially symmetric fashion around the circumference of the catheter for a uniform inflation if desired. Of course, less distortion under inflation may occur at or adjacent lumens such as 316'''C used for drug delivery, as these do not inflate.

The inflatable lumens 316'''A–B and 316'''D–N may be caused to inflate under influence of, e.g., an air compressor with a variable air delivery flow. Rapid pulses of air may be used to inflate the lumens 316'''A–B and 316'''D–N in a rapid and repeated fashion. By so doing, the outer walls defining these lumens move rapidly into and out of the bloodstream around the catheter, inducing turbulence. Preferably, the amplitude of the vibrations is large enough to move the outer walls defining the lumens out of the boundary layer and into the free stream of blood. This effect produces mixing which is used to enhance heat transfer. As it is important to induce mixing primarily near the heat transfer element, the area of appropriate wall thickness to allow for inflation need only be at, near, or adjacent the portion of the return catheter exterior wall adjacent the heat transfer element. In other words, the return catheter wall only requires substantial reduction near the heat transfer element. The remainder of the catheter wall may remain thick for strength and durability.

The supply catheter 310 may be constructed such that the same does not contact the interior of the distal end 308 of the heat transfer element, which may cause a subsequent stoppage of flow of the working fluid. Such construction may be via struts located in the return catheter 302 that extend radially inwards and secure the supply catheter 310 from longitudinal translations. Alternatively, struts may extend longitudinally from the distal end of the supply catheter 310 and hold the same from contacting the heat transfer element. This construction is similar to strut 112 shown in FIG. 11.

Figure 20:
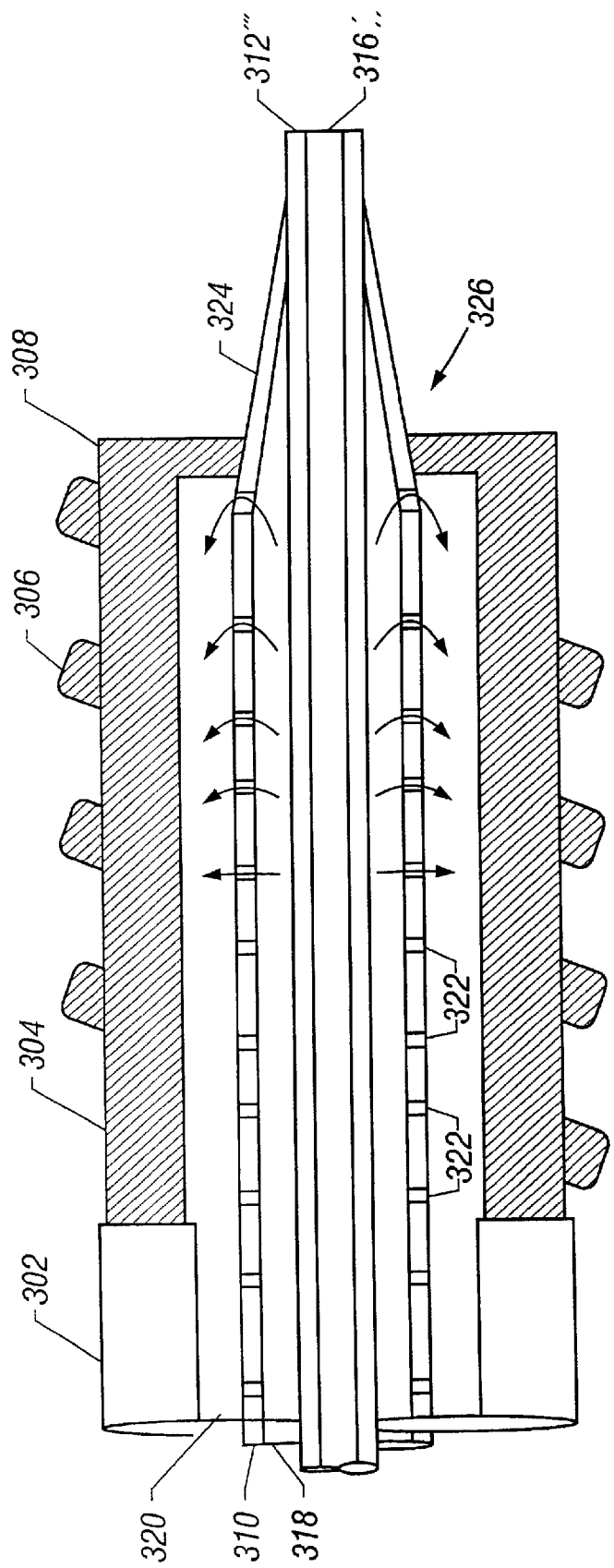
FIG. 20 is a front sectional view of a tenth embodiment of a catheter employing a heat transfer element according to the principles of the invention.

FIG. 20 shows an alternate method of accomplishing this goal. In FIG. 20, a heat transfer element 304' has an orifice 326 at a distal end 308. A supply catheter 310' is equipped with a drug delivery catheter 312' extending coaxially therein. The drug delivery catheter 312 may be formed of a solid material integral with supply catheter 310', or the two may be bonded after being constructed of separate pieces, or the two may remain separate during use, with a friction fit maintaining their positions with respect to each other. The supply catheter 310' is "in position" when a tapered portion 324 of the same is lodged in the hole 326 in the heat transfer element 304'. The tapered portion 324 should be lodged tightly enough to cause a strong friction fit so that working fluid does not leak through the hole 326. However, the tapered portion 324 should be lodged loosely enough to allow the supply catheter 310' to be removed from the heat transfer element 304' if continued independent use of the return catheter is desired.

The supply catheter 310' has a plurality of outlets 322. Outlets 322 are provided at points generally near or adjacent the distal end of the supply catheter 310'. The outlets are provided such that, when the supply catheter 310' is in position, the outlets generally face the heat transfer element 304'. In this way, the working fluid, emerging from the outlets 322, more directly impinges on the interior wall of the heat transfer element 304'. In particular, the working fluid exits the interior of the supply catheter and flows into a volume defined by the exterior of the supply catheter and the interior of the heat transfer element.

For clarity, FIG. 20 does not show the invaginations on the interior wall of the heat transfer element 304'. However, it will be understood that such invaginations may be present and may allow for enhanced heat transfer in combination with the emerging working fluid.

In the embodiments of FIGS. 10, 12, and 14–20, various types of catheter assemblies employing drug delivery catheters are described. In those embodiments, and particularly in the embodiments such as FIGS. 12, 15 and 20, in which a distal end of the drug delivery catheter protrudes substantially from the distal end of the remainder of the catheter assembly, a therapy may be performed in which the distal end of the catheter is embedded into a clot to be dissolved. An enzyme solution, such as a warm or cool enzyme solution, may then be sent directly into the clot to locally enhance the fibrinolytic activity.

In particular, the catheter may be placed as described above. In this procedure, however, the catheter is placed such that the tip of the protruding drug delivery catheter touches, is substantially near, or becomes embedded within the clot. An enzyme solution or other such drug is then delivered down the drug delivery catheter directly into the clot or into the volume of blood surrounding the clot. The enzyme solution may include tPA, streptokinase, urokinase, pro-urokinase, combinations thereof, and may be heated to enhance fibrinolytic activity. In a related embodiment, the solution may be a simple heated saline solution. The heated saline solution warms the clot, or the volume surrounding the clot, again leading to enhanced fibrinolytic activity.

In these procedures, it is advantageous to use embodiments of the invention in which the distal tip of the drug delivery catheter is substantially protruding, or is distal, from the remainder of the catheter assembly. In this way, the distal tip may be disposed adjacent to or within a clot without being obstructed by the remainder of the catheter assembly.

The heat transfer element 110 (FIG. 11) may employ any of the forms disclosed above, as well as variations of these forms. For example, the heat transfer element 110 may employ alternating helical ridges separated by flexible joints, the ridges creating sufficient mixing and/or surface area to enhance heat transfer between a working fluid and blood in the artery or vein. Alternatively, the heat transfer element 110 may be inflatable and may have sufficient surface area such that the heat transfer due to conduction alone is sufficient to provide the requisite heat transfer. Details of the heat transfer element 110 are omitted in FIG. 11 for clarity.

Figure 21:
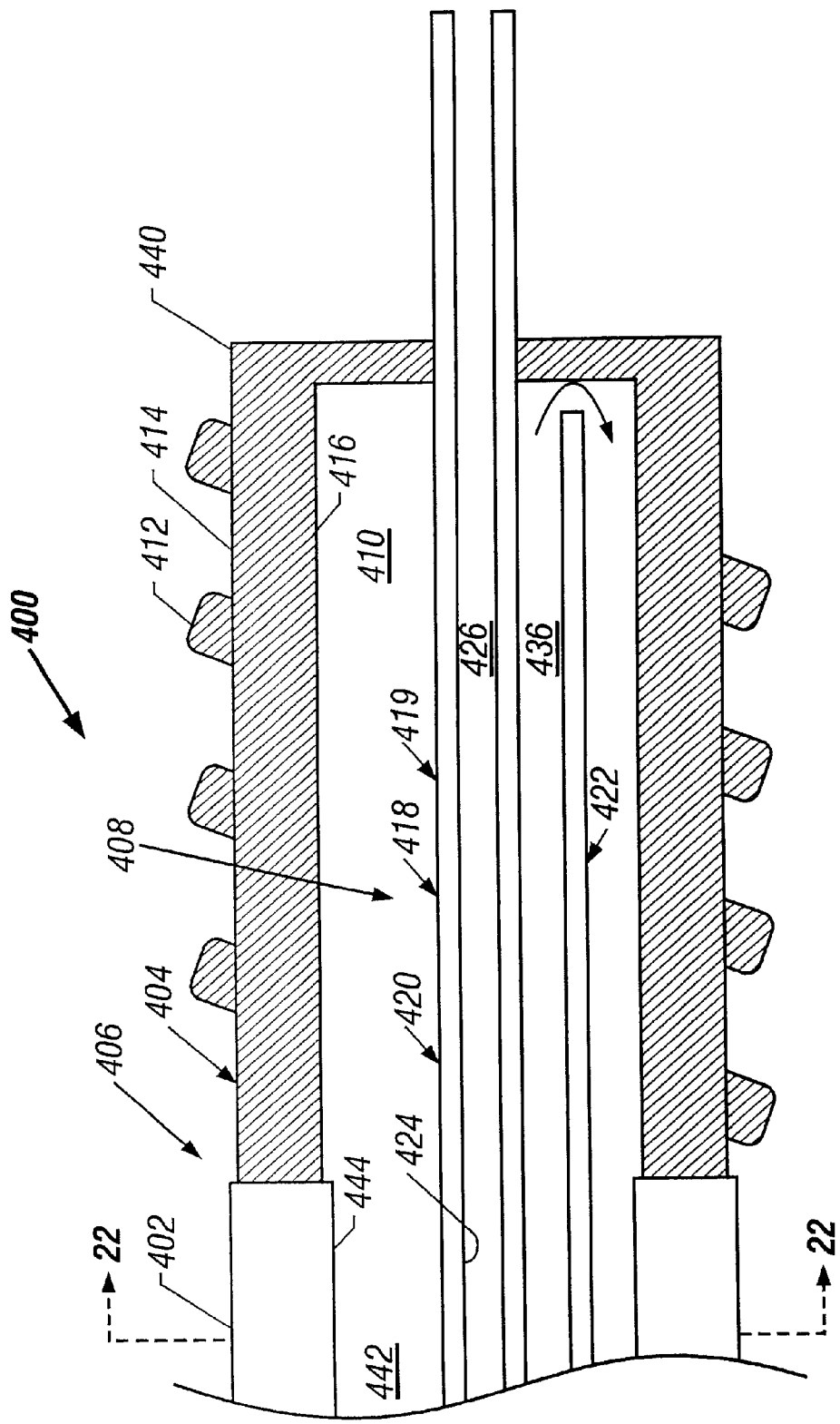
FIG. 21 is a front sectional view of a further embodiment of a catheter employing a heat transfer element according to the principles of the invention further employing a side-by-side lumen arrangement constructed in accordance with an embodiment of the invention.
Figure 22:
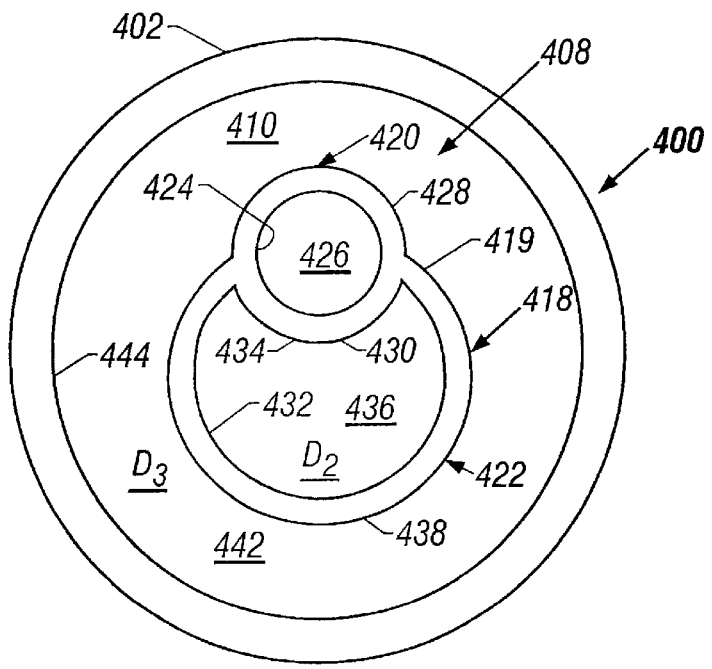
FIG. 22 is a cross-sectional view of the catheter of FIG. 21 taken along line 22—22 of FIG. 21.

With reference to FIGS. 21 and 22, a catheter 400 constructed in accordance with an alternative embodiment of the invention will now be described. The catheter 400 includes an elongated catheter body 402 with a heat transfer element 404 located at a distal portion 406 of the catheter body 402. The catheter 400 includes a multiple lumen arrangement 408 to deliver fluid to and from an interior 410 of the heat transfer element 404 and allow the catheter 400 to be placed into a blood vessel over a guidewire. The heat transfer element 404 includes turbulence-inducing invaginations 412 located on an exterior surface 414. Similar invaginations may be located on an interior surface 416 of the heat transfer element 404, but are not shown for clarity. Further, it should be noted that the heat transfer element 404 is shown with only four invaginations 412. Other embodiments may employ multiple elements connected by flexible joints or bellows as disclosed above. A single heat transfer element is shown in FIG. 21 merely for clarity. In an alternative embodiment of the invention, any of the other heat-transfer elements described herein may replace heat transfer element 406. Alternatively, the multi-lumen arrangement may be used to deliver fluid to and from the interior of an operative element(s) other than a heat-transfer-element such as, but without limitation, a catheter balloon, e.g., a dilatation balloon.

The catheter 400 includes an integrated elongated multiple lumen member such as a bi-lumen member 418 having a first lumen member 420 and a second lumen member 422. The bi-lumen member 418 has a substantially figure-eight cross-sectional shape (FIG. 22) and an outer surface 419 with the same general shape. The first lumen member 420 includes an interior surface 424 defining a first lumen or guide wire lumen 426 having a substantially circular cross-sectional shape. The interior surface 424 may be coated with a lubricious material to facilitate the sliding of the catheter 400 over a guidewire. The first lumen member 420 further includes a first exterior surface 428 and a second exterior surface 430. The first lumen 426 is adapted to receive a guide wire for placing the catheter 400 into a blood vessel over the guidewire in a well-known manner.

In FIGS. 21 and 22, the guide wire lumen 426 is not coaxial with the catheter body 402. In an alternative embodiment of the invention, the guide wire lumen 426 may be coaxial with the catheter body 402.

The second lumen member 422 includes a first interior surface 432 and a second interior surface 434, which is the same as the second exterior surface 430 of the first lumen member 420, that together define a second lumen or supply lumen 436 having a substantially luniform cross-sectional shape. The second lumen member 422 further includes an exterior surface 438. The second lumen 436 has a cross-sectional area $A_2$. The second lumen 436 is adapted to supply working fluid to the interior of the heat transfer element 404 to provide temperature control of a flow or volume of blood in the manner described above.

The second lumen member 422 terminates short of a distal end 440 of the catheter 400, leaving sufficient space for the working fluid to exit the supply lumen 436 so it can contact the interior surface 416 of the heat transfer element 404 for heat transfer purposes.

Figure 23:
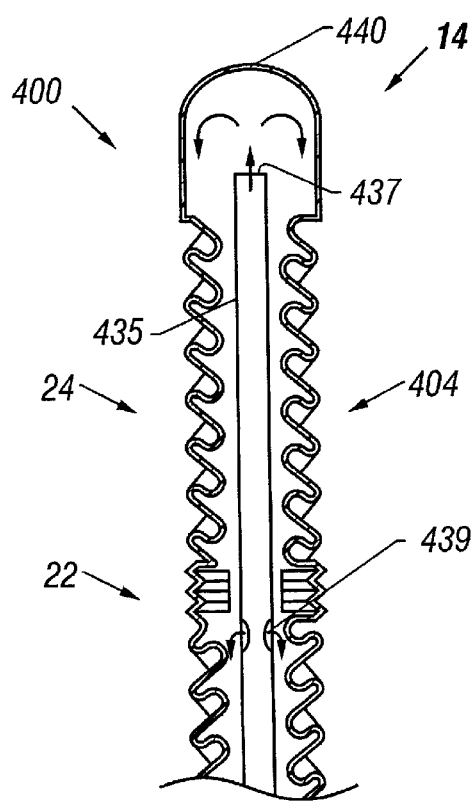
FIG. 23 is a front sectional view of a catheter employing a heat transfer element and lumen arrangement constructed in accordance with a further embodiment of the invention.

Although the second lumen member 422 is shown as a single supply lumen terminating adjacent the distal end 440 of catheter 400 to deliver working fluid at the distal end of the catheter 200, with reference to FIG. 23, in an alternative embodiment of the invention, a single supply lumen member 435 may include one or more outlet openings 437 adjacent the distal end 440 of the catheter 400 and one or more outlet openings 439 adjacent a mid-point along the interior length of the heat transfer element 404. This arrangement improves the heat transfer characteristics of the heat-transfer element 404 because fresh working fluid at the same temperature is delivered separately to each segment 22, 24 of the interior of the heat-transfer element 404 instead of in series.

Although two heat transfer segments 22, 24 are shown, it will be readily apparent that a number of heat transfer segments other than two, e.g., one, three, four, etc., may be used.

It will be readily apparent to those skilled in the art that in another embodiment of the invention, in addition to the one or more openings 437 in the distal portion of the heat transfer element 404, one or more openings at one or more locations may be located anywhere along the interior length of the heat transfer element 404 proximal to the distal portion.

Figure 24:
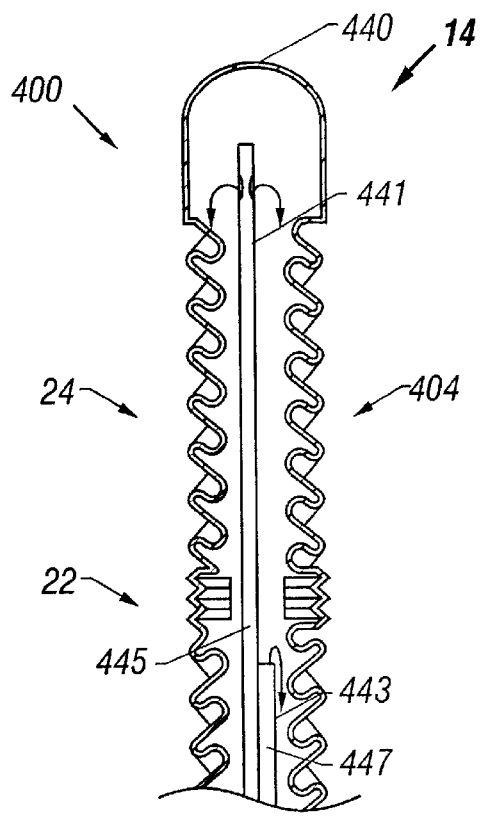
FIG. 24 is a front sectional view of a catheter employing a heat transfer element and lumen arrangement constructed in accordance with a still further embodiment of the invention.

With reference to FIG. 24, in an alternative embodiment of the invention, first and second supply lumen members 441, 443 define respective first and second supply lumens 445, 447 for supplying working fluid to the interior of the heat transfer element 404. The first supply lumen 441 terminates just short of the distal end 440 of the catheter 400 to deliver working fluid at the distal portion of the heat transfer element 404. The second supply lumen 443 terminates short of the distal portion of the catheter 400, for example, at approximately a mid-length point along the interior of the heat transfer element 404 for delivering working fluid to the second heat transfer segment 22. In an alternative embodiment of the invention, the second lumen member 443 may terminate anywhere along the interior length of the heat transfer element 404 proximal to the distal portion of the heat transfer element 404. Further, a number of supply lumens 443 greater than two may terminate along the interior length of the heat transfer element 404 for delivering a working fluid at a variety of points along the interior length of the heat transfer element 404.

With reference back to FIGS. 21 and 22, the bi-lumen member 418 is preferably extruded from a material such as polyurethane or Pebax. In an embodiment of the invention, the bi-lumen member is extruded simultaneously with the catheter body 402. In an alternative embodiment of the invention, the first lumen member 420 and second lumen member 422 are formed separately and welded or fixed together.

A third lumen or return lumen 442 provides a convenient return path for working fluid. The third lumen 442 is substantially defined by the interior surface 416 of the heat transfer element 404, an interior surface 444 of the catheter body 402, and the exterior surface 419 of the bi-lumen member 418. The inventors have determined that the working fluid pressure drop through the lumens is minimized when the third lumen 442 has a hydraulic diameter $D_3$ that is equal to 0.75 of the hydraulic diameter $D_2$ of the second lumen 436. However, the pressure drop that occurs when the ratio of the hydraulic diameter $D_3$ to the hydraulic diameter $D_2$ is substantially equal to 0.75, i.e., 0.75±0.10, works well. For flow through a cylinder, the hydraulic diameter D of a lumen is equal to four times the cross-sectional area of the lumen divided by the wetted perimeter. The wetted perimeter is the total perimeter of the region defined by the intersection of the fluid path through the lumen and a plane perpendicular to the longitudinal axis of the lumen. The wetted perimeter for the return lumen 442 would include an inner wetted perimeter (due to the outer surface 419 of the bi-lumen member 418) and an outer wetted perimeter (due to the interior surface 444 of the catheter body 402). The wetted perimeter for the supply lumen 436 would include only an outer wetted perimeter (due to the first and second interior surfaces 432, 434 of the bi-lumen member 418). Thus, the wetted perimeter for a lumen depends on the number of boundary surfaces that define the lumen.

The third lumen 442 is adapted to return working fluid delivered to the interior of the heat transfer element 404 back to an external reservoir or the fluid supply for recirculation in a well-known manner.

In an alternative embodiment, the third lumen 442 is the supply lumen and the second lumen 436 is the return lumen. Accordingly, it will be readily understood by the reader that adjectives such as "first," "second," etc. are used to facilitate the reader's understanding of the invention and are not intended to limit the scope of the invention, especially as defined in the claims.

In a further embodiment of the invention, the member 418 may include a number of lumens other than two such as, for example, 1, 3, 4, 5, etc. Additional lumens may be used as additional supply and/or return lumens, for other instruments, e.g., imaging devices, or for other purposes, e.g., inflating a catheter balloon or delivering a drug.

Heating or cooling efficiency of the heat transfer element 404 is optimized by maximizing the flow rate of working fluid through the lumens 436, 442 and minimizing the transfer of heat between the working fluid and the supply lumen member. Working fluid flow rate is maximized and pressure drop minimized in the present invention by having the ratio of the hydraulic diameter $D_3$ of the return lumen 442 to the hydraulic diameter $D_2$ of the supply lumen 436 equal to 0.75. However, a ratio substantially equal to 0.75, i.e., 0.75±10–20%, is acceptable. Heat transfer losses are minimized in the supply lumen 436 by minimizing the surface area contact made between the bi-lumen member 418 and the working fluid as it travels through the supply lumen member. The surface area of the supply lumen member that the supplied working fluid contacts is much less than that in co-axial or concentric lumens used in the past because the supplied working fluid only contacts the interior of one lumen member compared to contacting the exterior of one lumen member and the interior of another lumen member. Thus, heat transfer losses are minimized in the embodiments of the supply lumen in the multiple lumen member 418 of the present invention.

Figure 25:
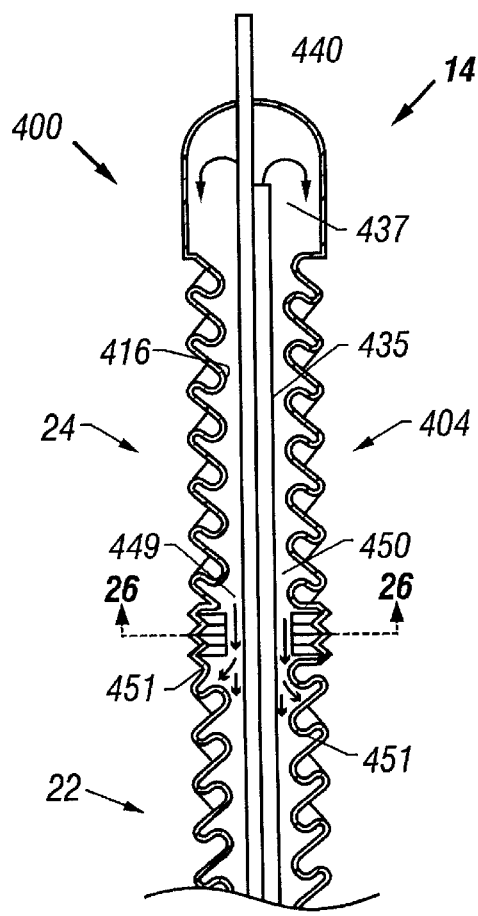
FIG. 25 is a front sectional view of a another embodiment of a catheter employing a heat transfer element according to the principles of the invention further employing a side-by-side lumen arrangement constructed in accordance with another embodiment of the invention.
Figure 26:
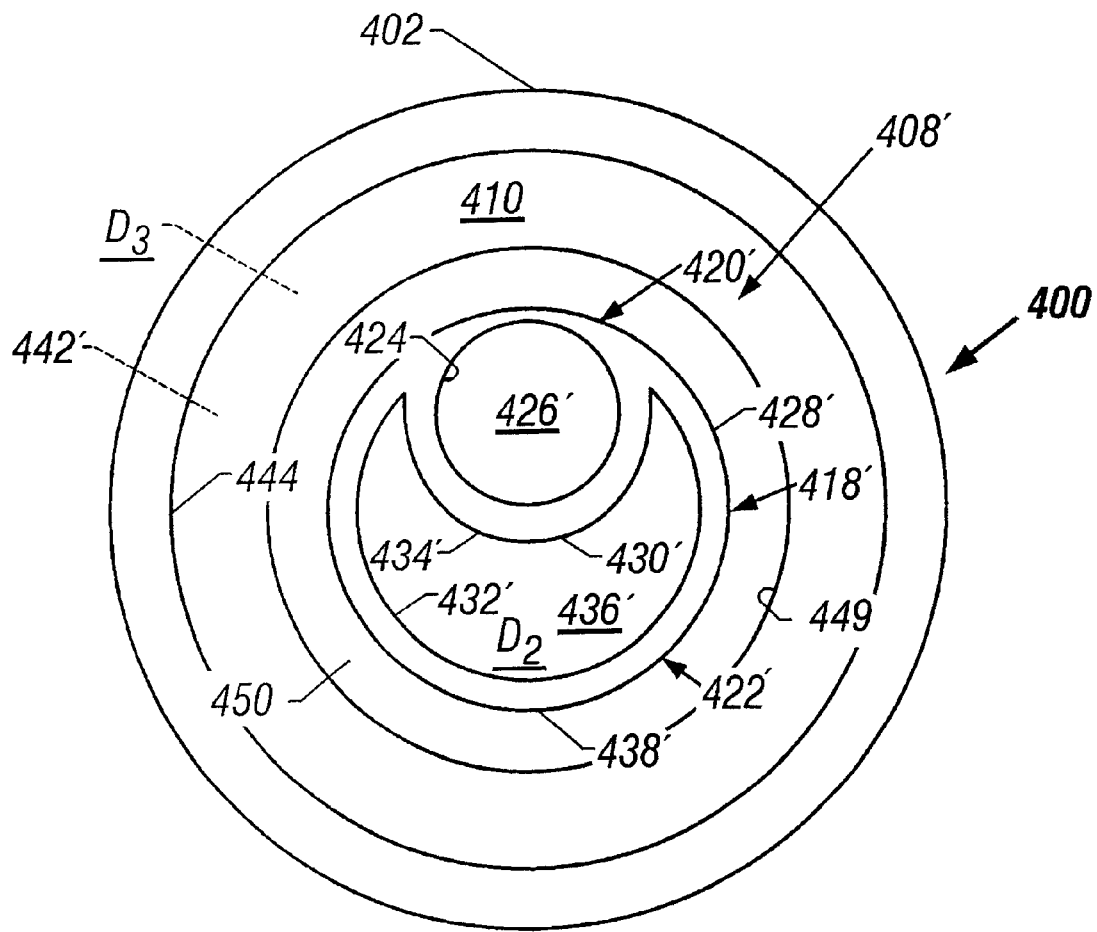
FIG. 26 is a cross-sectional view of the heat transfer element illustrated in FIG. 25 taken along line 26—26 of FIG. 25.

It will be readily apparent to those skilled in the art that the supply lumen 436 and the return lumen 442 may have cross-sectional shapes other than those shown and described herein and still maintain the desired hydraulic diameter ratio of substantially 0.75. With reference to FIGS. 25 and 26, an example of a catheter 400 including a supply lumen and a return lumen constructed in accordance with an alternative preferred embodiment of the invention, where the hydraulic diameter ratio of the return lumen to the supply lumen is substantially equal to 0.75 is illustrated. It should be noted, the same elements as those described above with respect to FIGS. 21 and 22 are identified with the same reference numerals and similar elements are identified with the same reference numerals, but with a (') suffix.

The catheter 400 illustrated in FIGS. 25 and 26 includes a multiple lumen arrangement 408' for delivering working fluid to and from an interior 410 of the heat transfer element 404 and allowing the catheter to be placed into a blood vessel over a guide wire. The multiple lumen arrangement 408' includes a bi-lumen member 418' with a slightly different construction from the bi-lumen member 418 discussed above with respect to FIGS. 21 and 22. Instead of an outer surface 419 that is generally figure-eight shaped, the bi-lumen member 418' has an outer surface 419' that is circular. Consequently, the third lumen 442' has an annular cross-sectional shape.

As discussed above, maintaining the hydraulic diameter ratio of the return lumen 436' to the supply lumen 442' substantially equal to 0.75 maximizes the working fluid flow rate through the multiple lumen arrangement 408'.

In addition, the annular return lumen 442' enhances the convective heat transfer coefficient within the heat transfer element 404, especially adjacent an intermediate segment or bellows segment 449. Working fluid flowing through the annular return lumen 442', between the outer surface 419' of the bi-lumen member 418' and the inner surface 416 of the heat transfer element, encounters a restriction 450 caused by the impingement of the bellows section 449 into the flow path. Although the impingement of the bellows section 449 is shown as causing the restriction 450 in the flow path of the return lumen 442', in an alternative embodiment of the invention, the bi-lumen member 418' may create the restriction 450 by being thicker in this longitudinal region of the bi-lumen member 418'. The distance between the bi-lumen member 418' and the bellows section 449 is such that the characteristic flow resulting from a flow of working fluid is at least of a transitional nature.

For a specific working fluid flux or flow rate (cc/sec), the mean fluid velocity through the bellows section restriction 450 will be greater than the mean fluid velocity obtained through the annular return lumen 442' in the heat transfer segment 22, 24 of the heat transfer element 404. Sufficiently high velocity through the bellows section restriction 450 will result in wall jets 451 directed into the interior portion 416 of the heat transfer segment 22. The wall jets 451 enhance the heat transfer coefficient within the helical heat transfer segment 22 because they enhance the mixing of the working fluid along the interior of the helical heat transfer segment 22. Increasing the velocity of the jets 451 by increasing the working fluid flow rate or decreasing the size of the restriction 450 will result in a transition closer to the jet exit and greater mean turbulence intensity throughout the helical heat transfer segment 22. Thus, the outer surface 419' of the bi-lumen member 418', adjacent the bellows 449, and the inner surface of the bellows 449 form means for further enhancing the transfer of heat between the heat transfer element 404 and the working fluid, in addition to that caused by the interior portion 416 of the helical heat transfer segment 22.

In an alternative embodiment of the invention, as described above, the heat transfer element may include a number of heat transfer segments other than two, i.e., 1, 3, 4, etc., with a corresponding number of intermediate segments, i.e., the number of heat transfer segments minus one.

The embodiment of the multiple lumen arrangement 418 discussed with respect to FIGS. 21 and 22 would not enhance the convective heat transfer coefficient as much as the embodiment of the multiple lumen arrangement 418' discussed with respect to FIGS. 25 and 26 because working fluid would preferentially flow through the larger areas of the return lumen 442, adjacent the junction of the first lumen member 420 and second lumen member 422. Thus, high-speed working fluid would have more contact with the outer surface 419 of the bi-lumen member 418 and less contact with the interior portion of 416 heat transfer element 404. In contrast, the annular return lumen 442' of the multiple lumen arrangement 418' causes working fluid flow to be axisymmetric so that significant working flow contacts all areas of the helical segment equally.

The invention has been described with respect to certain embodiments. It will be clear to one of skill in the art that variations of the embodiments may be employed in the method of the invention. Accordingly, the invention is limited only by the scope of the appended claims.

What is claimed is:

1. A method of manufacturing a catheter assembly for heating or cooling a surrounding fluid in a vascular feeding vessel, comprising:

extruding an elongated catheter body;

locating a heat transfer element including an interior at a distal portion of the catheter body;

extruding an integrated elongated bi-lumen member including a first lumen adapted to receive a guide wire and a second lumen, the second lumen comprising either a supply lumen to deliver a working fluid to an interior of the heat transfer element or a return lumen to return a working fluid from the interior of the heat transfer element;

providing said integrated bi-lumen member substantially within said elongated catheter body so that a third lumen is formed, said third lumen comprising either a supply lumen to deliver a working fluid to an interior of the heat transfer element or a return lumen to return a working fluid from the interior of the heat transfer element.

2. The method of claim 1, wherein said second lumen has a hydraulic diameter and said third lumen has a hydraulic diameter, and the ratio of the hydraulic diameter of the second lumen to the hydraulic diameter of the third lumen is substantially equal to 0.75.

3. The method of claim 1, wherein the step of providing said integrated bi-lumen member substantially within said elongated catheter body includes simultaneously extruding said integrated bi-lumen member substantially within said elongated catheter body.

4. A method of manufacturing a catheter assembly, comprising:

extruding an elongated catheter body;

locating an operative element including an interior at a distal portion of the catheter body;

extruding an integrated elongated bi-lumen member including a first lumen adapted to receive a guide wire and a second lumen, the second lumen comprising either a supply lumen to deliver a working fluid to an interior of the operative element or a return lumen to return a working fluid from the interior of the operative element;

providing said integrated bi-lumen member substantially within said elongated catheter body so that a third lumen is formed, said third lumen comprising either a supply lumen to deliver a working fluid to an interior of the operative element or a return lumen to return a working fluid from the interior of the operative element.

5. The method of claim 4, wherein said second lumen has a hydraulic diameter and said third lumen has a hydraulic diameter, and the ratio of the hydraulic diameter of the second lumen to the hydraulic diameter of the third lumen is substantially equal to 0.75.

6. The method of claim 4, wherein the step of providing said integrated bi-lumen member substantially within said elongated catheter body includes simultaneously extruding said integrated bi-lumen member substantially within said elongated catheter body.

7. A method of manufacturing a catheter assembly, comprising:

extruding an elongated catheter body;

locating an operative element including an interior at a distal portion of the catheter body;

extruding an integrated elongated bi-lumen member including a first lumen adapted to receive a guide wire and a second lumen, the second lumen comprising either a supply lumen to deliver a working fluid to an interior of the operative element or a return lumen to return a working fluid from the interior of the operative element, the integrated elongated bi-lumen member including a circular outer surface;

providing said integrated bi-lumen member substantially within said elongated catheter body so that a third lumen is formed, said third lumen comprising either a supply lumen to deliver a working fluid to an interior of the operative element or a return lumen to return a working fluid from the interior of the operative element.

8. The method of claim 7, wherein said second lumen has a hydraulic diameter and said third lumen has a hydraulic diameter, and the ratio of the hydraulic diameter of the second lumen to the hydraulic diameter of the third lumen is substantially equal to 0.75.

9. The method of claim 7, wherein the step of providing said integrated bi-lumen member substantially within said elongated catheter body includes simultaneously extruding said integrated bi-lumen member substantially within said elongated catheter body.

* * * * *